(12) United States Patent
Osawa et al.

(10) Patent No.: US 7,954,778 B2
(45) Date of Patent: Jun. 7, 2011

(54) OPHTHALMIC SURGERY SUPPORT DEVICE

(75) Inventors: Koji Osawa, Anjo (JP); Masanori Hangai, Kyoto (JP)

(73) Assignee: Nidek Co., Ltd., Gamagori-shi (JP)

( * ) Notice: Subject to any disclaimer, the term of this patent is extended or adjusted under 35 U.S.C. 154(b) by 372 days.

(21) Appl. No.: 12/227,378

(22) PCT Filed: May 16, 2007

(86) PCT No.: PCT/JP2007/060052
§ 371 (c)(1),
(2), (4) Date: Dec. 15, 2008

(87) PCT Pub. No.: WO2007/135918
PCT Pub. Date: Nov. 29, 2007

(65) Prior Publication Data
US 2010/0168762 A1 Jul. 1, 2010

(30) Foreign Application Priority Data
May 18, 2006 (JP) ................................. 2006-138919

(51) Int. Cl.
*E04G 3/00* (2006.01)
(52) U.S. Cl. .................................. 248/278.1; 74/490.11
(58) Field of Classification Search ............... 248/278.1, 248/279.1, 280.11; 74/490.11; 606/130; 623/111
See application file for complete search history.

(56) References Cited

U.S. PATENT DOCUMENTS
6,684,129 B2 * 1/2004 Salisbury et al. ............. 700/245
2005/0109903 A1 * 5/2005 Strauss et al. ............. 248/280.11
2010/0114099 A1 * 5/2010 Patwardhan ..................... 606/80
2010/0214534 A1 * 8/2010 Kuebler et al. ............... 351/206
2010/0298843 A1 * 11/2010 Blumenkranz ................ 606/130
2010/0331858 A1 * 12/2010 Simaan et al. ................ 606/130
2011/0023651 A1 * 2/2011 Cooper ....................... 74/490.02

FOREIGN PATENT DOCUMENTS
| JP | B2 2642047 | 8/1997 |
| JP | A-9-276289 | 10/1997 |
| JP | A-2000-350735 | 12/2000 |
| JP | B2 3151422 | 4/2001 |
| JP | B2 3181608 | 7/2001 |
| JP | A 2006-26229 | 2/2006 |
| WO | WO 03/022336 A1 | 3/2003 |

* cited by examiner

*Primary Examiner* — Ramon O Ramirez
(74) *Attorney, Agent, or Firm* — Oliff & Berridge, PLC

(57) ABSTRACT

An ophthalmic surgery support comprising a moving mechanism for holding a surgical instrument to be movable in Z-axis direction, a tilting mechanism for holding the moving mechanism so that a surgical instrument can be tilted in an arbitrary direction about a specified point that is to be positioned to a wound opening and positioned on the Z-axis, and a tilt fixing mechanism for fixing the tilt of the surgical instrument by the tilting mechanism, wherein the tilting mechanism has a rough-motion tilting mechanism, a fine-motion tilting mechanism finer in tilting range than the rough-motion tilting mechanism, a tilt switching mechanism for switching the tilt of the surgical instrument by the rough-motion tilting mechanism to that by the fine-motion tilting mechanism, and a resistance imparting means for imparting resistance for damping the tilting operation of the surgical instrument by the fine-motion tilting mechanism than that by the rough-motion tilting mechanism.

9 Claims, 20 Drawing Sheets

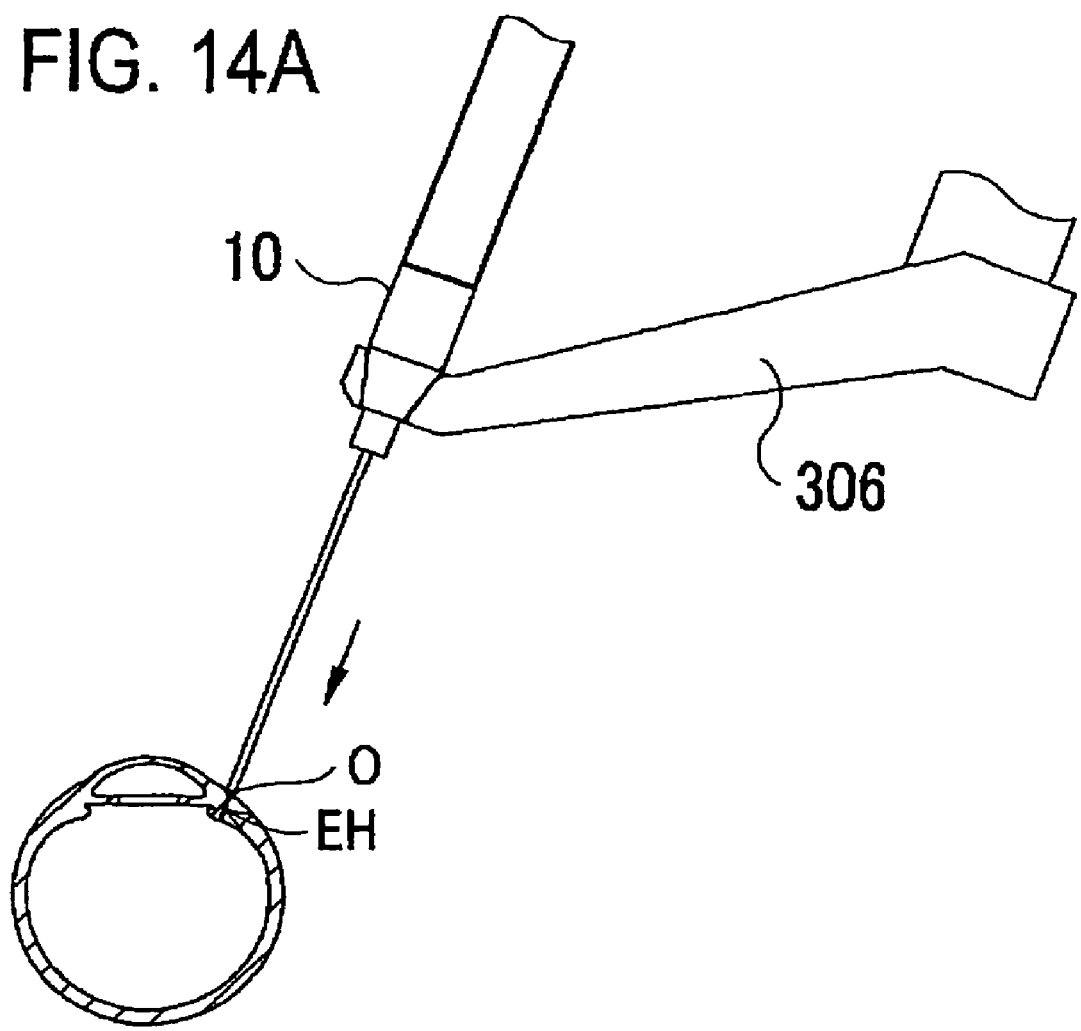

OPHTHALMIC SURGERY SUPPORT DEVICE

CROSS-REFERENCE TO RELATED APPLICATIONS

This is a national phase application based on the PCT International Patent Application No. PCT/JP2007/060052 filed on May 16, 2007, the entire contents of which are incorporated herein by reference.

TECHNICAL FIELD

The present invention relates to an ophthalmic surgery support device for assisting an operator in the operation of a surgical instrument in order to position a tip end of the surgical instrument to a fine location in an eye in which the surgical instrument is to be inserted through a wound opening formed in an eyeball of a patient.

BACKGROUND ART

As ophthalmic surgeries, there is a surgery to be performed by positioning a tip end of a cannula which is an surgical instrument to a blood clot of a blood vessel having a diameter of 0.1 mm to 0.2 mm existing in a retina of an eye fundus and puncturing the blood vessel or by positioning a tip end of a surgical instrument such as forceps, scissors, and tweezers to a fine affected part of a fundus (retina) and treating the affected part. Usually, an operator inserts the tip end of the surgical instrument in the eye through a wound opening formed in a sclera of an eyeball of a patient, positions the tip end of the surgical instrument to the affected part while observing the affected part through a microscope or the like, and treats the affected part with the surgical instrument. It is therefore preferable to make an accurate and easy positioning operation to position the tip end of the surgical instrument to the fine affected part.

DISCLOSURE OF INVENTION

Problems to be Solved by the Invention

The present invention has a purpose to provide an ophthalmic surgery support device whereby a surgical instrument can be easily operated and a tip end of the surgical instrument can be positioned accurately and readily to a fine location in an eye.

Means for Solving the Problems

To achieve the above purpose, the invention has the following configurations.

The present invention provides an ophthalmic surgery support device for assisting an operator in an operation of a surgical instrument in order to position a tip end of the surgical instrument to be inserted in an eye through a wound opening formed in an eyeball of a patient to a fine location in the eye, the device comprising: a moving mechanism for holding the surgical instrument movably in a Z axis direction that is a longitudinal direction of the surgical instrument to be inserted in the eye; a tilting mechanism for holding the moving mechanism so that the surgical instrument is tiltable in an arbitrary direction about a predetermined point which is located on a Z axis and is positioned to the wound opening; and a tilt locking mechanism for locking tilt of the surgical instrument tilted by the tilting mechanism, wherein the tilting mechanism comprises: a rough-motion tilting mechanism; a fine-motion tilting mechanism providing a finer tilt range than the rough-motion tilting mechanism; a tilt switching mechanism for switching tilt of the surgical instrument by the rough-motion tilting mechanism to tilt of the surgical instrument by the fine-motion tilting mechanism; and a resistance imparting means for imparting resistance to make a tilting operation of the surgical instrument by the fine-motion tilting mechanism heavier than a tilting operation of the surgical instrument by the rough-motion tilting mechanism.

In the ophthalmic surgery support device according to the present invention, preferably, the tilt locking mechanism comprises a rough-motion-tilting locking mechanism for locking the tilt of the surgical instrument tilted by the rough-motion tilting mechanism; and a fine-motion-tilting locking mechanism for locking the tilt of the surgical instrument tilted by the fine-motion tilting mechanism, the tilt switching mechanism for switching the tilt of the surgical instrument by the rough-motion tilting mechanism to the tilt of the surgical instrument by the fine-motion tilting mechanism when the tilt of the surgical instrument is locked by the rough-motion-tilting locking mechanism.

In the ophthalmic surgery support device according to the present invention, preferably, the tilting mechanism comprises a first tilting mechanism for holding the moving mechanism so as to tiltable about a first axis passing the predetermined point, and a second tilting mechanism for holding the first tilting mechanism so as to tiltable about a second axis intersecting the first axis at the predetermined point, the tilt locking mechanism comprises a first tilt locking mechanism for locking the tilt of the surgical instrument tilted by the first tilt mechanism and a second tilt locking mechanism for locking the tilt of the surgical instrument tilted by the second tilting mechanism, each of the first and second tilting mechanisms includes the rough-motion tilting mechanism, the fine-motion tilting mechanism, the tilt switching mechanism, and the resistance imparting means, and each of the first and second tilt locking mechanism has a rough-motion-tilting locking mechanism and a fine-motion-tilting locking mechanism.

In the ophthalmic surgery support device according to the present invention, preferably, at least one of the rough-motion-tilting locking mechanism and the fine-motion-tilting locking mechanism includes a brake mechanism utilizing pressure of air from a pump.

Preferably, the ophthalmic surgery support device according to the present invention further comprises a signal input unit for inputting a command signal to operate each of the rough-motion-tilting locking mechanism and the fine-motion-tilting locking mechanism, and a control unit for controlling operation of each locking mechanism based on the command signal from the signal input unit.

In the ophthalmic surgery support device according to the present invention, preferably, the signal input unit includes a footswitch provided with a plurality of switches, and the footswitch is used in common as a footswitch of a different ophthalmic apparatus.

In the ophthalmic surgery support device according to the present invention, preferably, the moving mechanism comprises: a rough-motion moving mechanism; a fine-motion moving mechanism for providing a finer movable range than the rough-motion moving mechanism; and a movement switching mechanism for switching movement of the surgical instrument by the rough-motion moving mechanism to movement of the surgical instrument by the fine-motion moving mechanism.

Preferably, the ophthalmic surgery support device according to the present invention further comprises: a rotating mechanism for holding the surgical instrument so as to be rotatable about the Z axis; and a rotation locking mechanism for locking the rotation of the surgical instrument.

Preferably, the ophthalmic surgery support device according to the present invention further comprises a three-dimensional moving mechanism for moving the tilting mechanism in three dimensions.

According to the invention, a surgical instrument can be operated easily, and a tip end of the surgical instrument can be positioned accurately and readily to a fine location in an eye.

BRIEF DESCRIPTION OF DRAWINGS

FIG. 14A is a view to explain operations in a surgery;

BEST MODE FOR CARRYING OUT THE INVENTION

Figure 1:
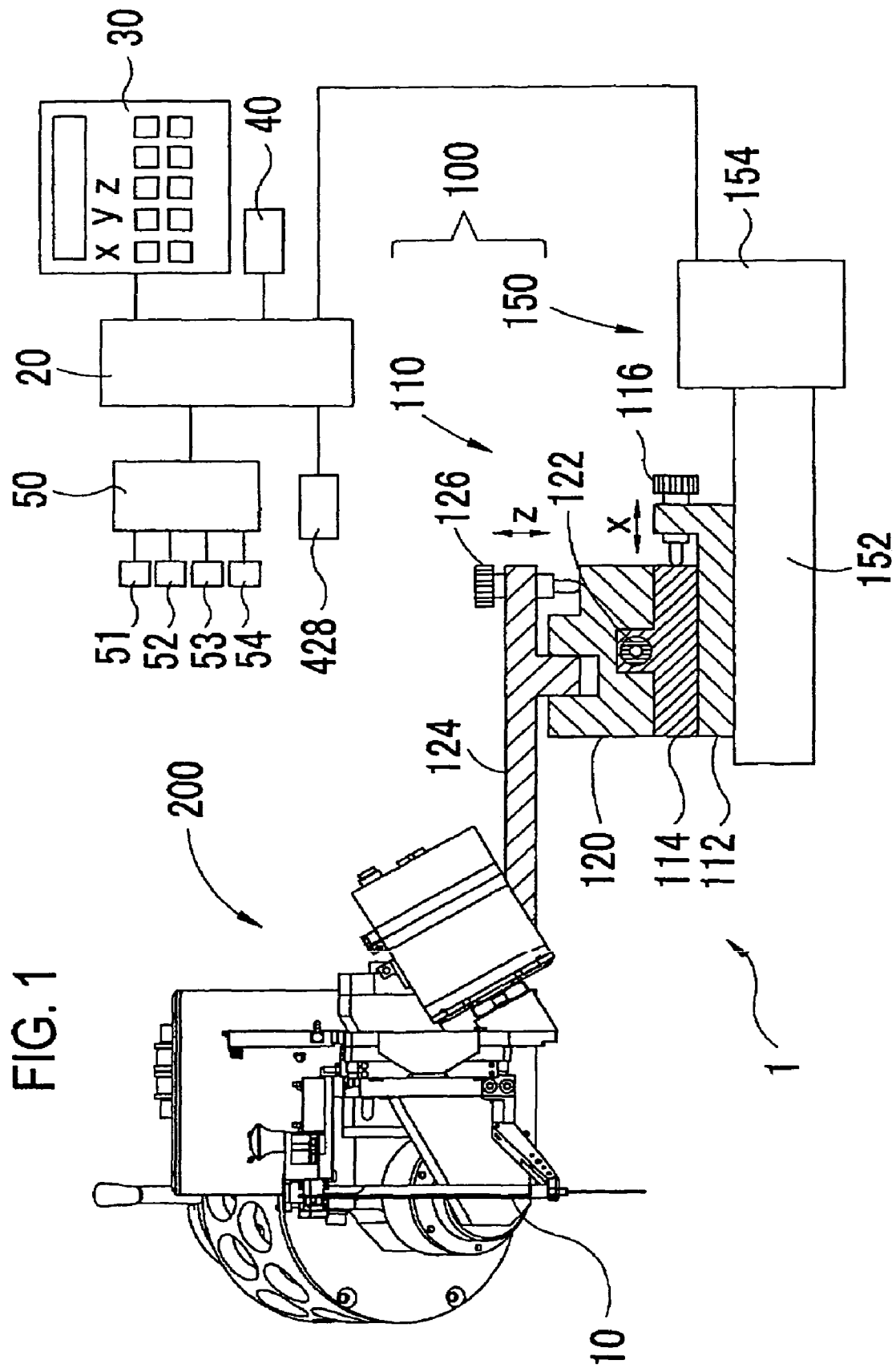
FIG. 1 is a schematic configuration view of an ophthalmic surgery support device in a preferred embodiment of the invention.

A detailed description of a preferred embodiment of the present invention will now be given referring to the accompanying drawings. FIG. 1 is a schematic configuration view of an ophthalmic surgery support device 1 in the embodiment of the present invention. The surgery support device 1 includes an extraocular moving unit 100 for positioning a surgical instrument 10 outside an eye and an intraocular positioning unit 200 for assisting an operator to operate the surgical instrument 10.

The moving unit 100 has a mechanism for holding the positioning unit 200 so as to be movable in an x-axis direction (a lateral direction on a drawing sheet of FIG. 1), a y-axis direction (a direction perpendicular to the drawing sheet of FIG. 1), and a z-axis direction (a vertical direction on the drawing sheet of FIG. 1). The moving unit 100 in this embodiment includes a three-dimensional fine adjustment unit 110 for precisely adjusting the positioning unit 200 in the x, y, and z-axis directions and a three-dimensional rough adjustment unit 150 for roughly adjusting the positioning unit 200 in the x, y, and z-axis directions.

The fine adjustment unit 110 includes moving mechanisms such as a fixed base 112, a first movable base 114 movable in the x-axis direction relative to the base 112, a micrometer 116 for moving the base 114, a second movable base 120 movable in the y-axis direction relative to the base 114, a micrometer 122 for moving the base 120, an arm 124 that is movable in the z-axis direction relative to the base 120 and supports the positioning unit 200, and a micrometer 126 for moving the arm 124.

The rough adjustment unit 150 includes an arm 152 on which the fine adjustment unit 110 is mounted, and a moving unit 154 for moving the arm 152 in the x, y, and z-axis directions. The moving unit 154 has moving mechanisms such as a slide mechanism and a motor. By such a mechanism, the movement is allowed and locked based on a command signal inputted with a joystick or the like. The mechanism may be a manually operated mechanism.

A drive speed of the motor constituting the rough adjustment unit 150 can be changed. Accordingly, the fine adjustment unit 110 and the rough adjustment unit 150 can be integrally configured.

Figure 2:
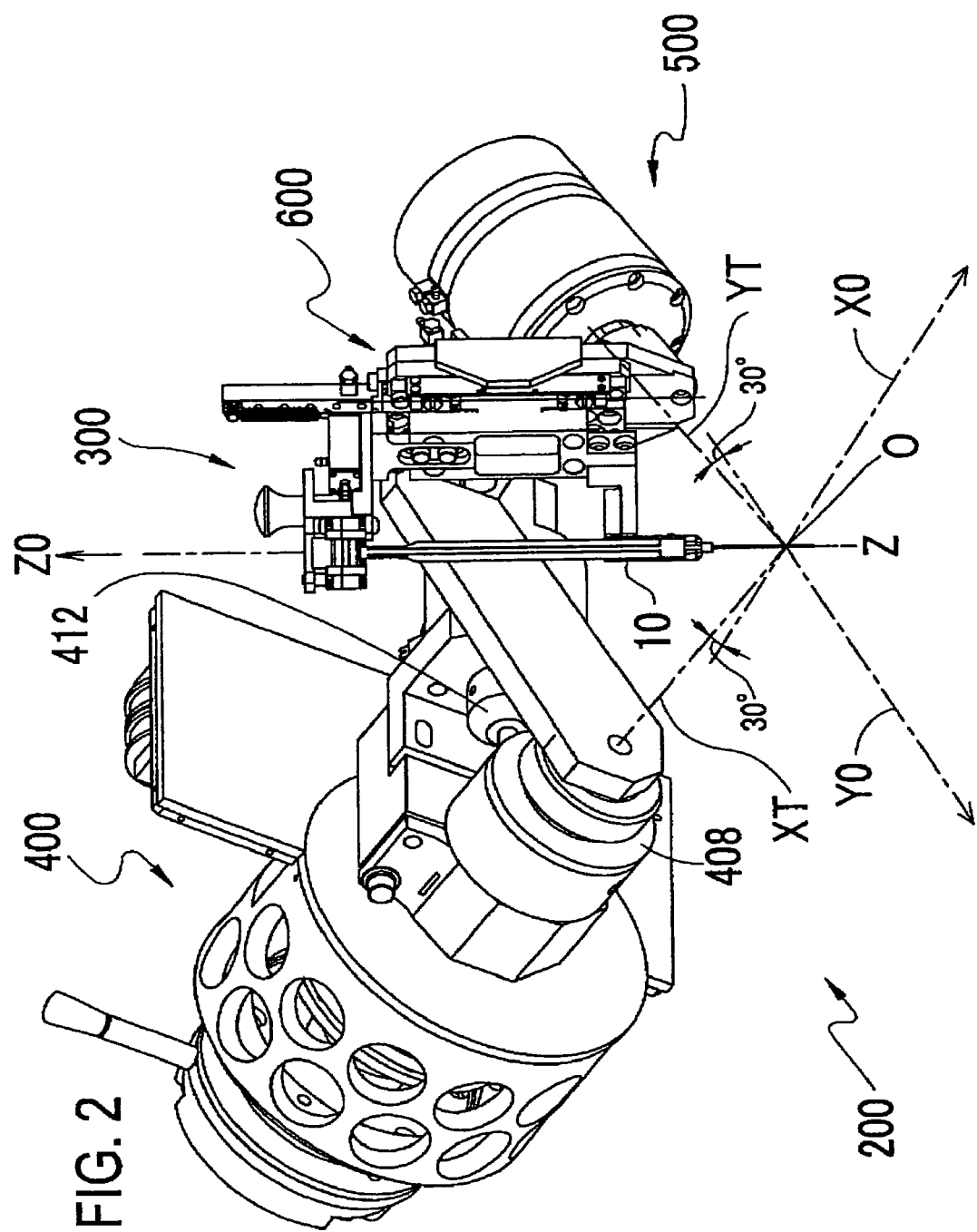
FIG. 2 is an external view showing a schematic configuration of an intraocular positioning unit.

FIG. 2 is an external view showing a schematic configuration of the positioning unit 200. The positioning unit 200 includes a holding unit 300 for holding the surgical instrument 10, a first tilting unit 400 and a second tilting unit 500 for two-dimensionally tilting the surgical instrument 10 held by the holding unit 300, and a Z moving unit 600 for holding the holding unit 300 so as to be movable in a longitudinal axis of the surgical instrument 10, that is, in the Z-axis direction. In FIG. 2, it is assumed that a vertical Z axis is a Z0 axis, a predetermined point located on the Z axis and below the Z moving unit 600 by a predetermined distance is a tilt center point (operation point) O, and two axes passing the point O and intersecting each other on a plane orthogonal to the Z0 axis are an X0 axis and a Y0 axis. The first and second tilting units 400 and 500 constitute a tilting unit for holding the Z moving unit 600 so that the surgical instrument 10 can be tilted two-dimensionally about the point O.

Figure 3:
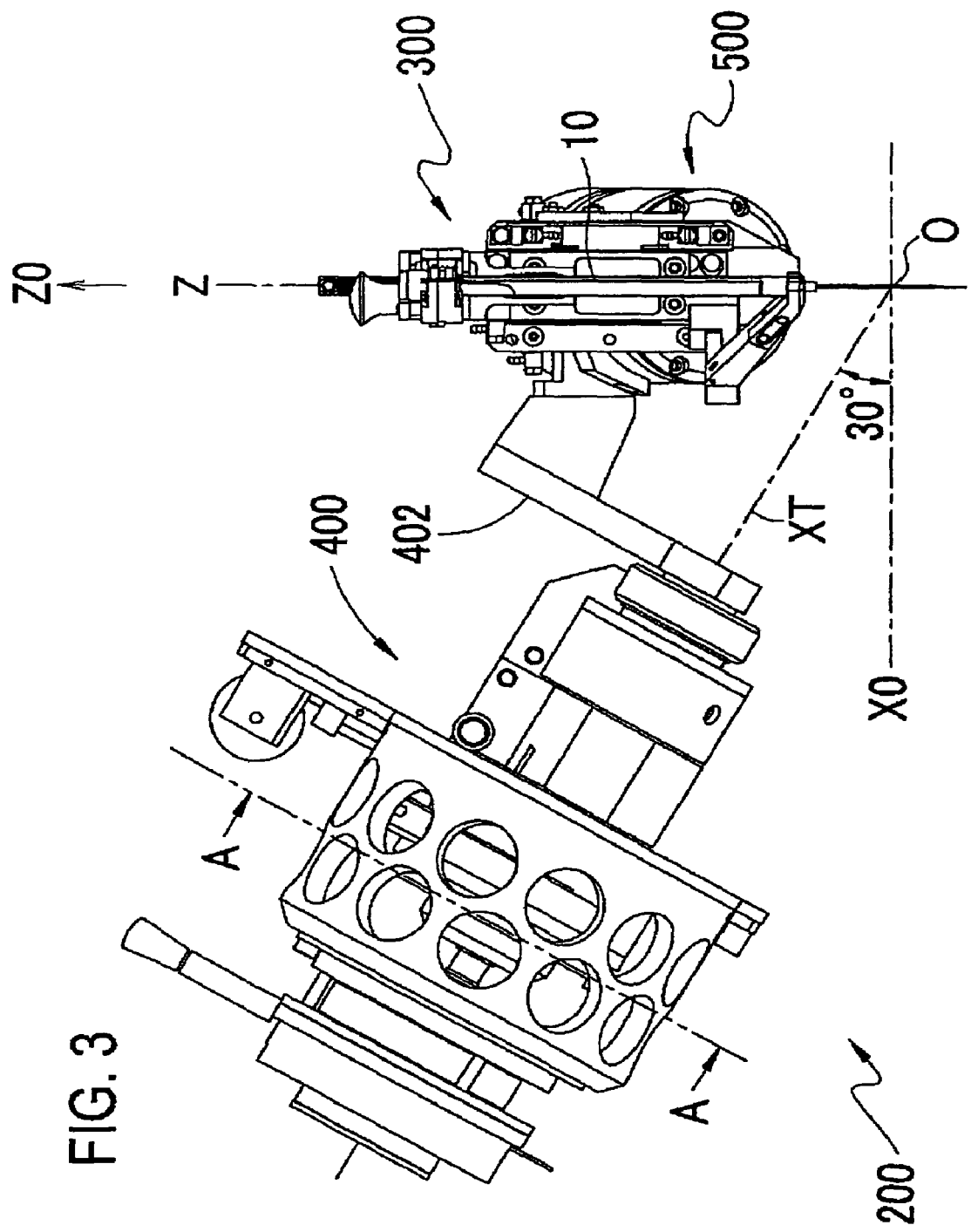
FIG. 3 is another external view showing the schematic configuration of the intraocular positioning unit.

FIG. 3 is an external view showing a schematic configuration of the positioning unit 200, viewed from a direction (a Y0 axis direction) perpendicular to an X0-Z0 plane in FIG. 2. The first tilting unit 400 holds the second tilting unit 500 so as to be rotatable (tiltable) about a first tilt axis XT passing the point O. The first tilt axis XT is located on the X0-Z0 plane and tilted at an angle of 30° from the X0 axis (60° from the Z0 axis) relative to the point O. The second tilting unit 500 is attached to a holding arm 402 rotatable about the first tilt axis XT.

Figure 4:
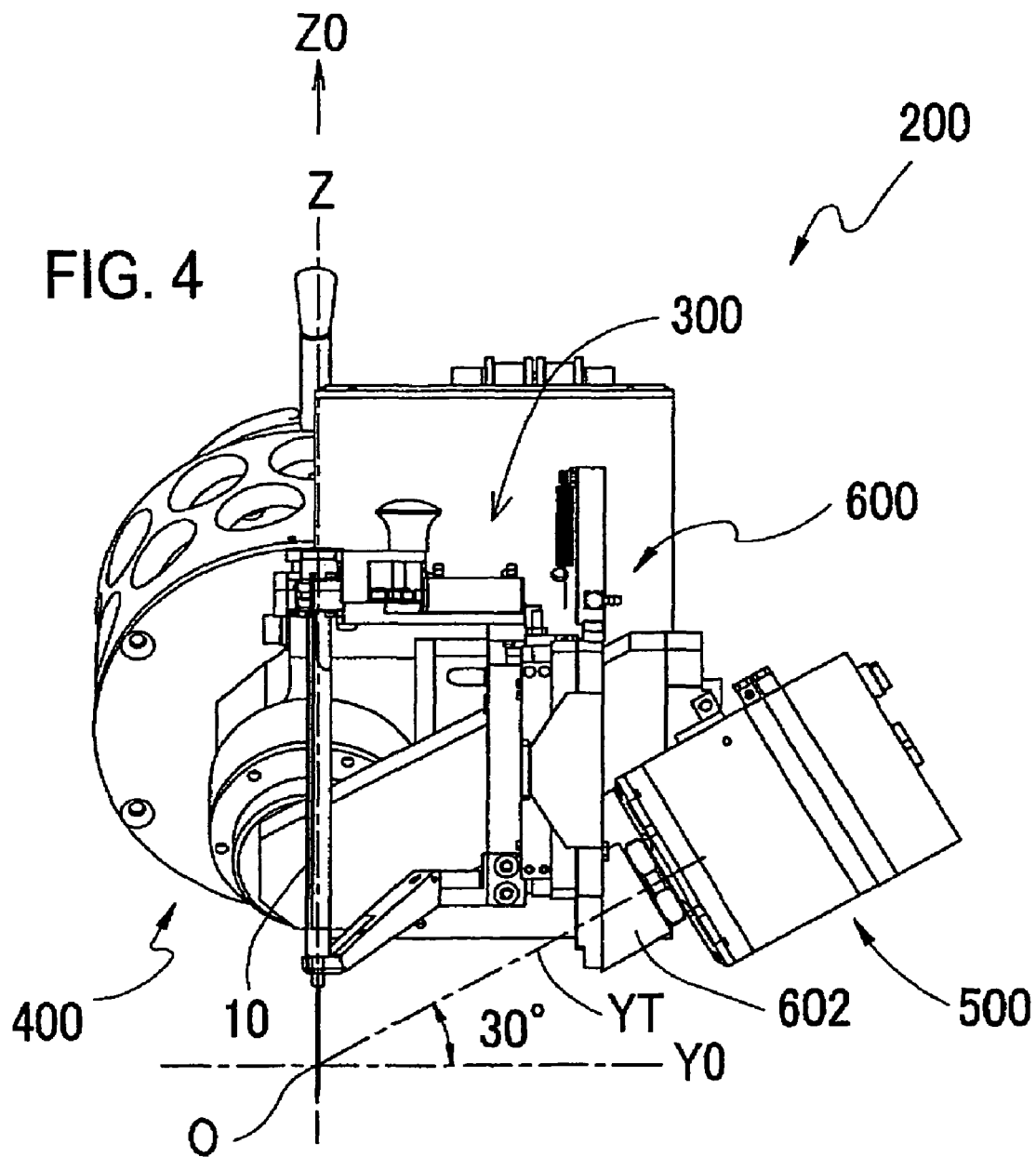
FIG. 4 is another external view showing the schematic configuration of the intraocular positioning unit.

FIG. 4 is another external view showing the schematic configuration of the positioning unit 200, viewed from a direction (an X0 axis direction) perpendicular to a Y0-Z0 plane in FIG. 2. The second tilting unit 500 holds the holding unit 300 so as to be rotatable (tiltable) about a second tilt axis YT passing the point O. The second tilt axis YT is located on the Y0-Z0 plane and tilted at an angle of 30° from the Y0 axis (60° from the Z0 axis) relative to the point O. The Z moving unit 600 is attached to a holding block 602 rotatable about the second tilt axis YT.

Figure 5:
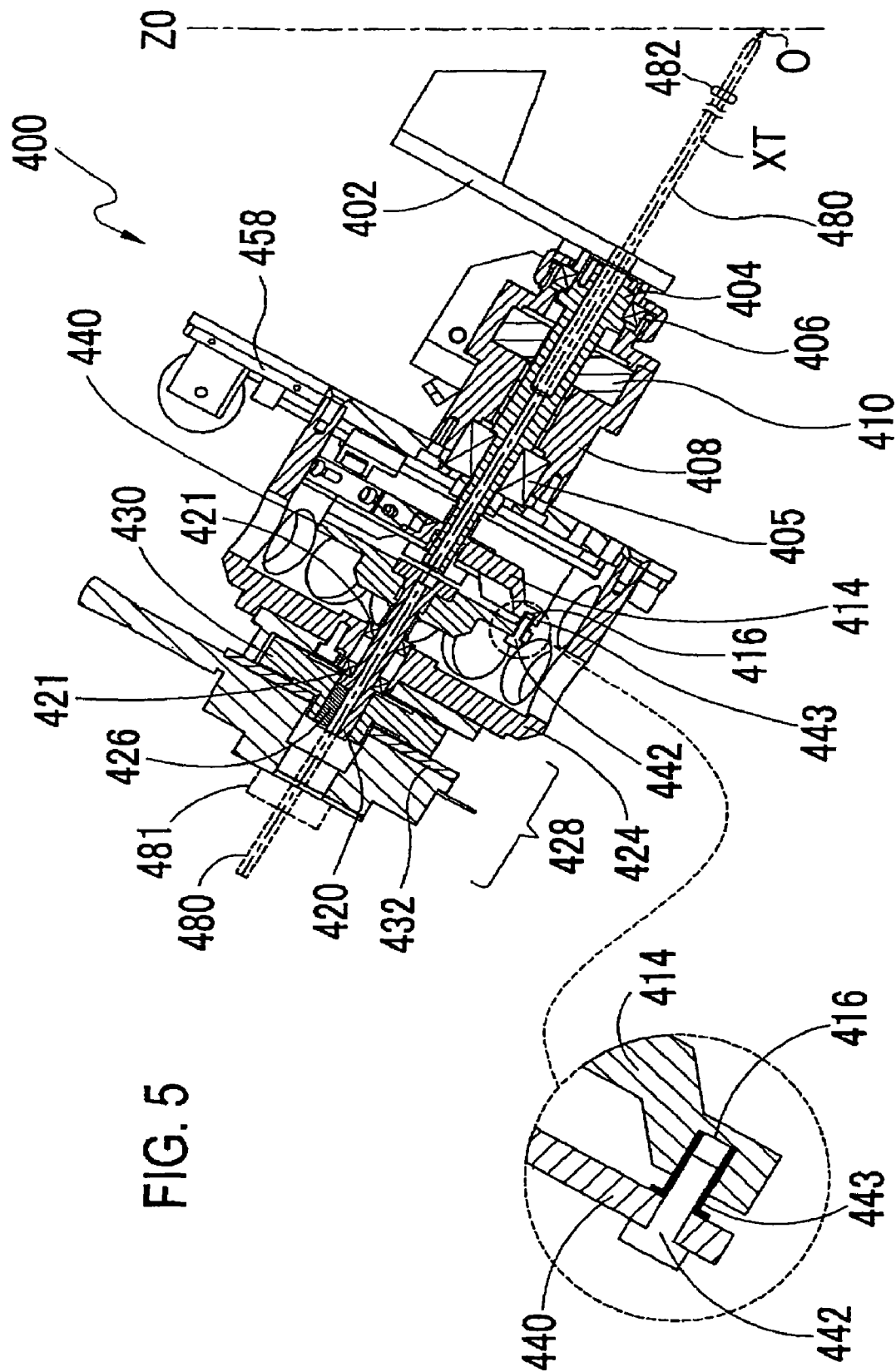
FIG. 5 is a sectional view showing a schematic configuration of a first tilting unit.

FIG. 5 is a sectional view showing a schematic configuration of the first tilting unit 400 taken along the X0-Z0 plane.

A hollow first fine-motion shaft 404 is held in a housing 408 through bearings 405 and 406 so as to be coaxial with the first tilt axis XT and rotatable (tiltable) about the first tilt axis XT. An arm 402 is fixed at a front end of the first fine-motion shaft 404. A friction joint 410 is attached between the housing 408 and the first fine-motion shaft 404. The friction joint 410 is arranged to lock or unlock (release the lock of) the first fine-motion shaft 404 with respect to the housing 408 by tightening or loosening a pressure screw not shown. The first fine-motion shaft 404 is locked by large frictional force generated by the friction joint 410. The pressure screw is tightened or loosened by a pneumatically-driven rotary actuator 412 attached to the outside of the housing 408. The rotary actuator 412 is supplied with compressed air from a compressed-air supply pump 50 through a tube. The compressed air is supplied or released (or reduced in pressure) by operation of an electromagnetic valve 53 controlled by a control unit 20 based on a switch signal (a command signal) of an operation panel 30 or a footswitch 40. For locking the first fine-motion shaft 404, another device utilizing friction and others may be adopted.

Behind the first fine-motion shaft 404, a hollow first rough-motion shaft 420 is held in a housing 424 through two bearings 421 so as to be coaxial with the first tilt axis XT and rotatable (tiltable) about the first tilt axis XT. The first fine-motion shaft 404 and the first rough-motion shaft 420 are configured independently of each other. A rotatable range of the first rough-motion shaft 420 (a tiltable range of the surgical instrument 10) is determined to be relatively wide and preferably cause the surgical instrument 10 to tilt at a tilt angle of ±55° or more from a vertical position thereof, and more preferably, at a tilt angle of ±60° or more.

A rotor 430 of an electromagnetic clutch 428 is fixed on the first rough-motion shaft 420 with a key 426. The electromagnetic clutch 428 has an armature 432 which normally presses the rotor 430 and will be separated from the rotor 430 by electromagnetic force generated by energization. The first rough-motion shaft 420 is locked or unlocked (released from the locked state) by pressing or separating of the rotor 430. The pressing or separating of the rotor 430 is executed by the electromagnetic clutch 428 controlled by the control unit 20 based on the switch signal (the command signal) of the operation panel 30 or the footswitch 40. For locking the first rough-motion shaft 420, another device may also be adopted.

A flange 414 is attached to a rear end of the first fine-motion shaft 404. A flange 440 is attached to a front end of the first rough-motion shaft 420. The flange 414 is formed with a hole 416. The flange 440 is attached with a boss 442 engaging in the hole 416. The hole 416 is larger in diameter than the boss 442. In a clearance between the hole 416 and the boss 442, a viscoelastic member 443 such as silicone resin is inserted to impart resistance in order to make heavier (or damp) the rotation of the first fine-motion shaft 404 (the tilting of the surgical instrument 10). The hole 416 and the boss 442 serve to limit the rotatable angle of the first fine-motion shaft 404 about the first tilt axis XT to a smaller angle than the rotatable angle of the first rough-motion shaft 420 and to switch (change) the tiltable range of the surgical instrument 10 in at least two stages; a rough-motion range and a fine-motion range. When the first fine-motion shaft 404 is rotated about the first tilt axis XT while the first rough-motion shaft 420 is locked, the flange 414 is also rotated, deforming the viscoelastic member 443 placed in the clearance between the boss 442 and the hole 416. Accordingly, the flange 414 can be rotated only in a deformable range of the viscoelastic member 443. When the first rough-motion shaft 420 is locked by the controlled electromagnetic clutch 428, therefore, the first fine-motion shaft 404 can be rotated only in the deformable range of the viscoelastic member 443. In addition, reaction to external force (an operator's operation to tilt the surgical instrument 10) also becomes heavier (damp) by resistance of elasticity of the viscoelastic member 443 than in the case where the first rough-motion shaft 420 is not locked. This makes it possible to facilitate fine positioning of the tip end of the surgical instrument 10. When the first rough-motion shaft 420 is locked and also the first fine-motion shaft 404 is locked by the controlled electromagnetic valve 53, the surgical instrument 10 is completely fixed against tilting (rotation) about the first tilt axis XT.

The movable range of the first fine-motion shaft 404 is preferably determined, as a range for allowing fine positioning of the tip end of the surgical instrument 10, to be within ±5° relative to the locked first rough-motion shaft 420. For instance, when the tip end of the surgical instrument 10 is located at a distance of 25 mm from the point O (when the tip end of the surgical instrument 10 inserted in the eye is to be positioned to the fundus), the movable range of the first fine-motion shaft 404 is determined to be within about ±2.3° to allow the tip end of the surgical instrument 10 to tilt in a range of ±1.0 mm, more preferably determined to be within ±1.15° to allow the tip end of the surgical instrument 10 to tilt in a range of ±0.5 mm.

As a unit for imparting resistance to damp the rotation of the first fine-motion shaft 404 (the tilting of the surgical instrument 10), another configuration instead of the viscoelastic member 443 may be adopted in which a pinion is provided as a rotary damper in the flange 440 and a spur gear is provided as a damper guide engaging the pinion in the flange 414. Alternatively, another configuration that imposes resistance by pressure of air from the pump 50 may also be adopted.

Figure 6:
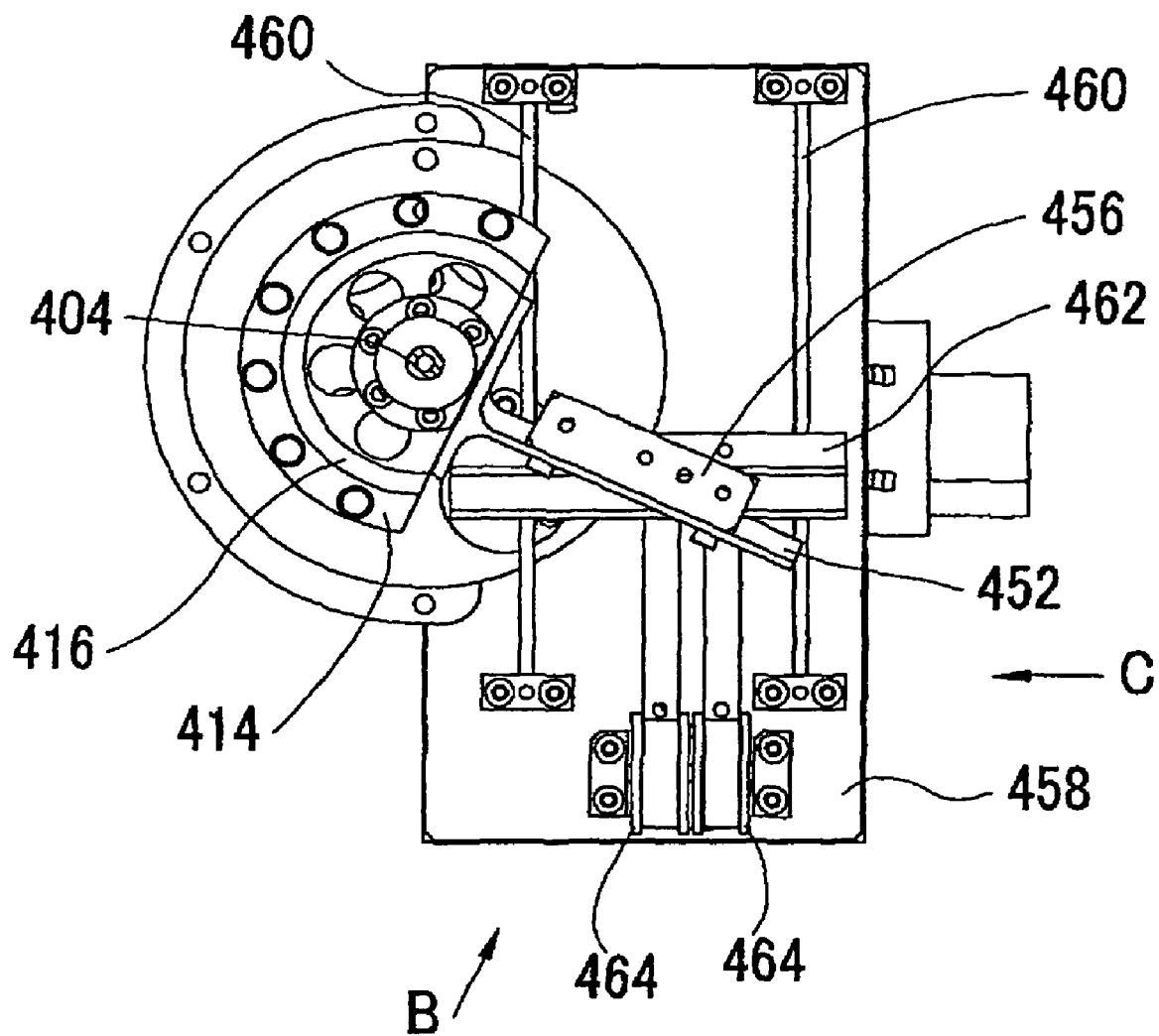
FIG. 6 is a view to explain a balance mechanism of the first tilting unit.
Figure 7:
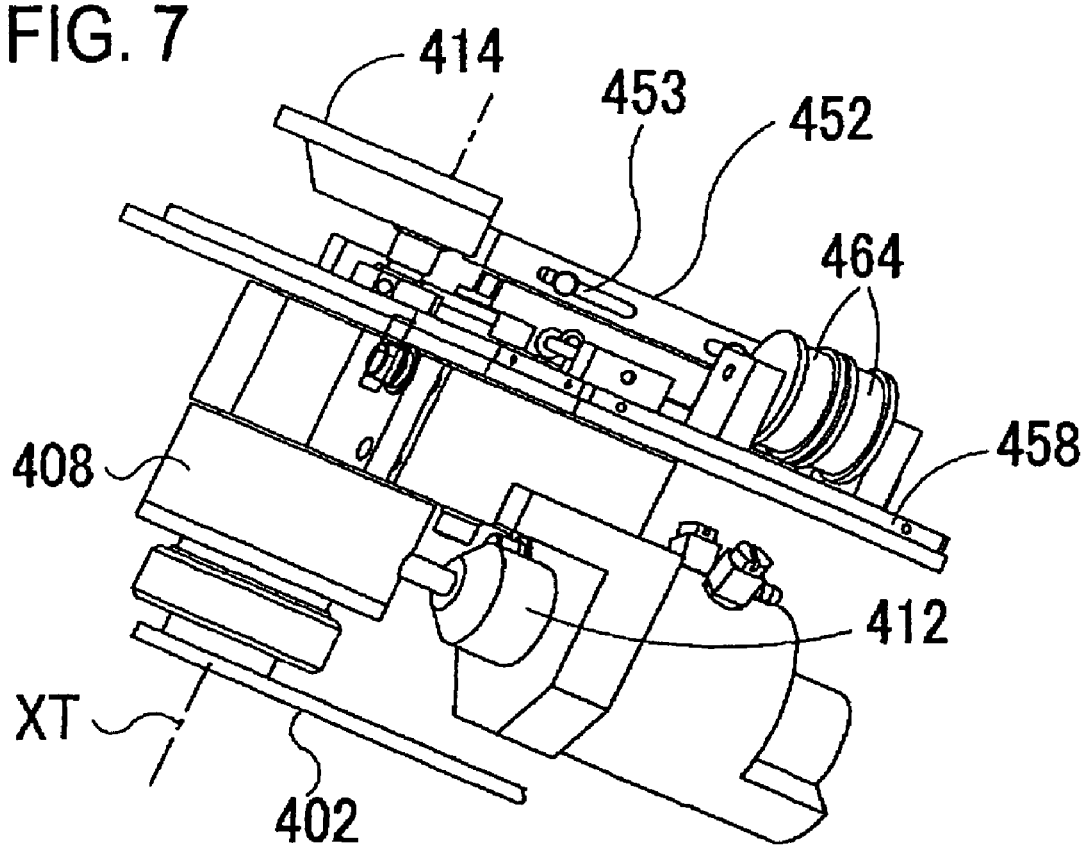
FIG. 7 is another view to explain the balance mechanism of the first tilting unit.
Figure 8:
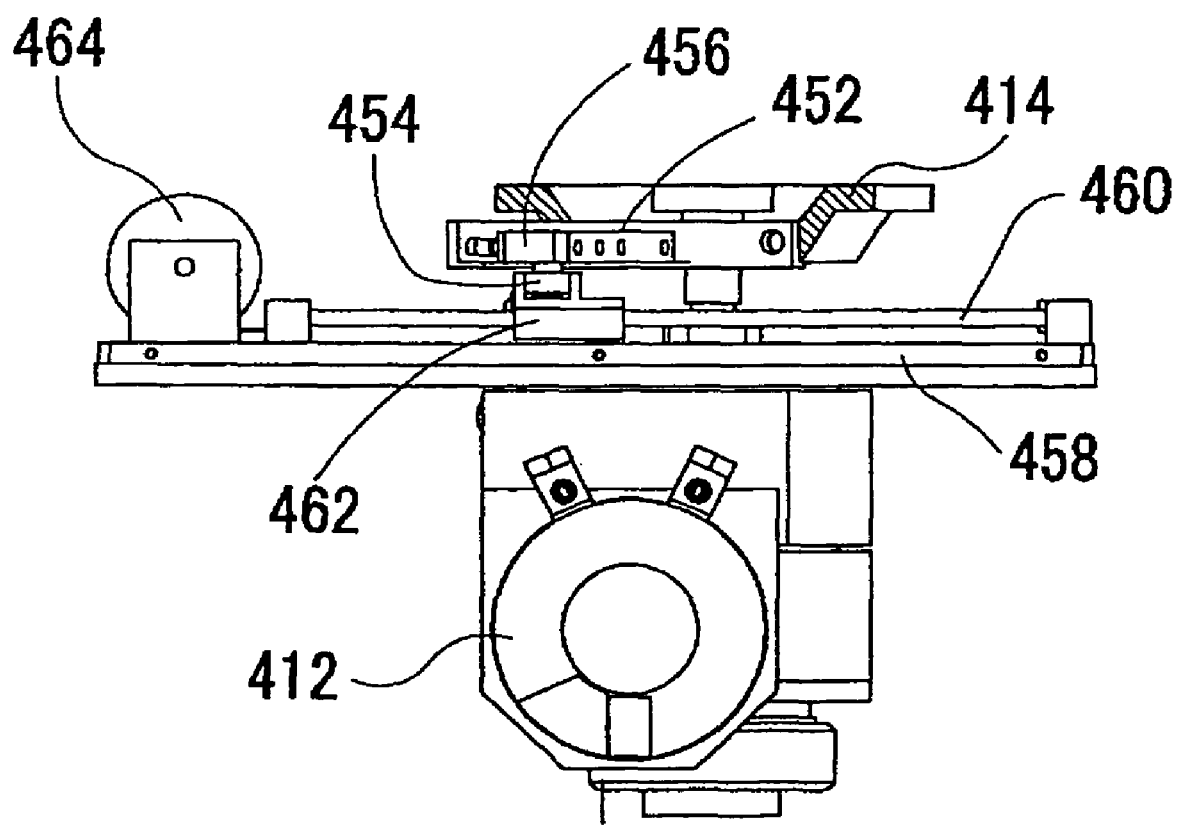
FIG. 8 is another view to explain the balance mechanism of the first tilting unit.

FIGS. 6, 7, and 8 views showing a balance mechanism of the first tilting unit 400 for rotation about the first tilt axis XT. FIG. 6 is a sectional view along a line A-A in FIG. 3, FIG. 7 is an external view seen from a direction B in FIG. 6, and FIG. 8 is an external view seen from a direction C in FIG. 6. This balance mechanism is to reduce gravity moment that acts when the surgical instrument 10 is tilted (rotated) about the first tilt axis XT.

A holding arm 452 is attached to the flange 414. The arm 452 extends in the same angular direction as the second tilting unit 500 fixed to the arm 402 and is rotatable integral with the first fine-motion shaft 404. A fixed block 456 to which a cam follower 454 is fixed is secured in a long hole 453 formed in the arm 452 with a screw so that a distance in a radius direction is adjustable. On the fixed base 458 fixed to the housing 408, two linear-motion guides 460 are fixed. A movable block 462 is movable along the linear-motion guides 460 and constantly receives, through the cam follower 454, a moment load resulting from the gravity of the second tilting unit 500. On the base 458, two constant load springs 464 are fixed. The springs 464 pull the block 462 to cancel the moment load imposed on the block 462. The position of the long hole 453 for fixing the block 456 to the arm 452 is adjusted to take a balance of the load.

In each hollow part of the first fine-motion shaft 404 and the first rough-motion shaft 420, a shaft 480 with a tapered tip is inserted as a positioning device for positioning the point O to the wound opening of the patient's eye.

Figure 9:
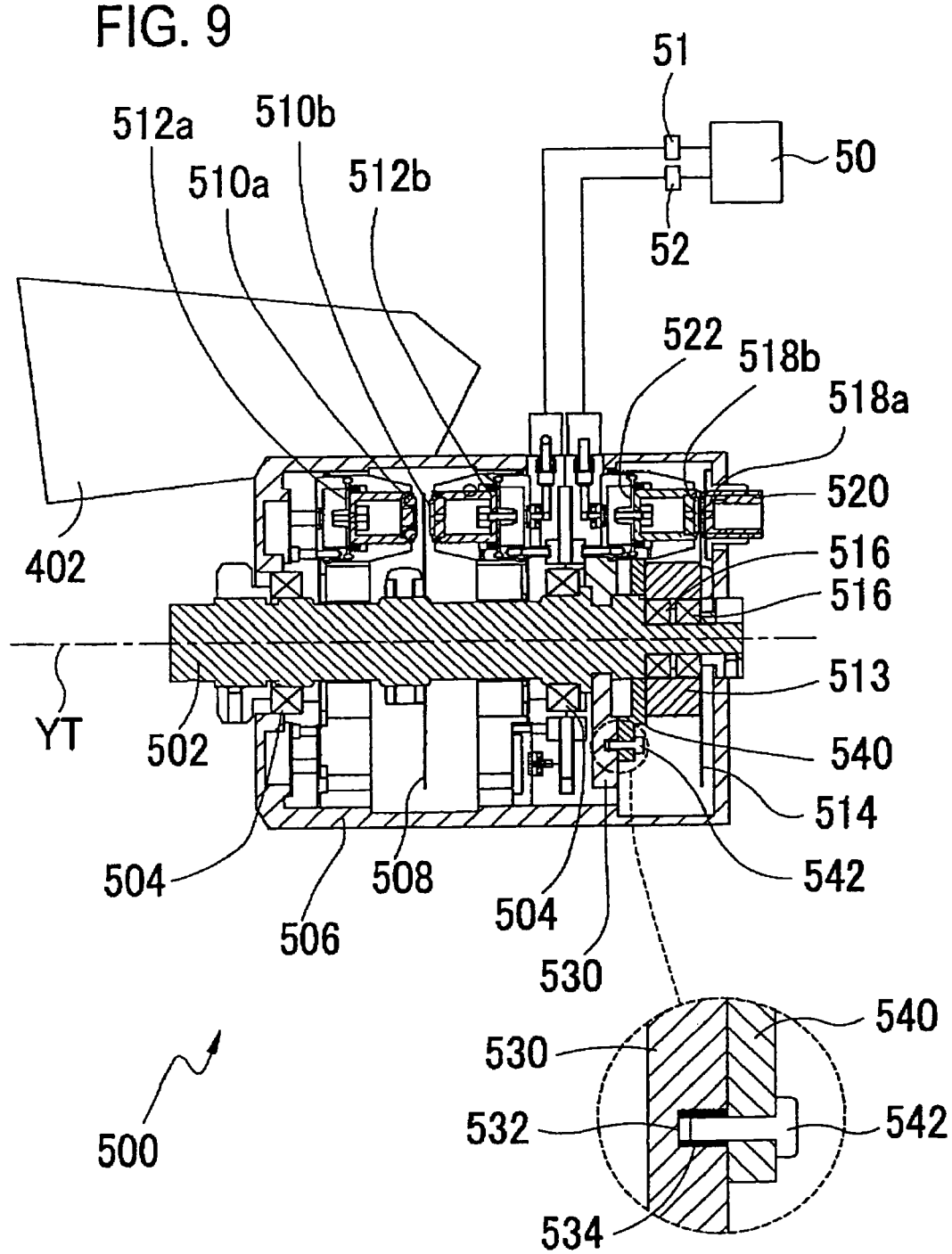
FIG. 9 is a sectional view showing a schematic configuration of a second tilting unit.
Figure 10A:
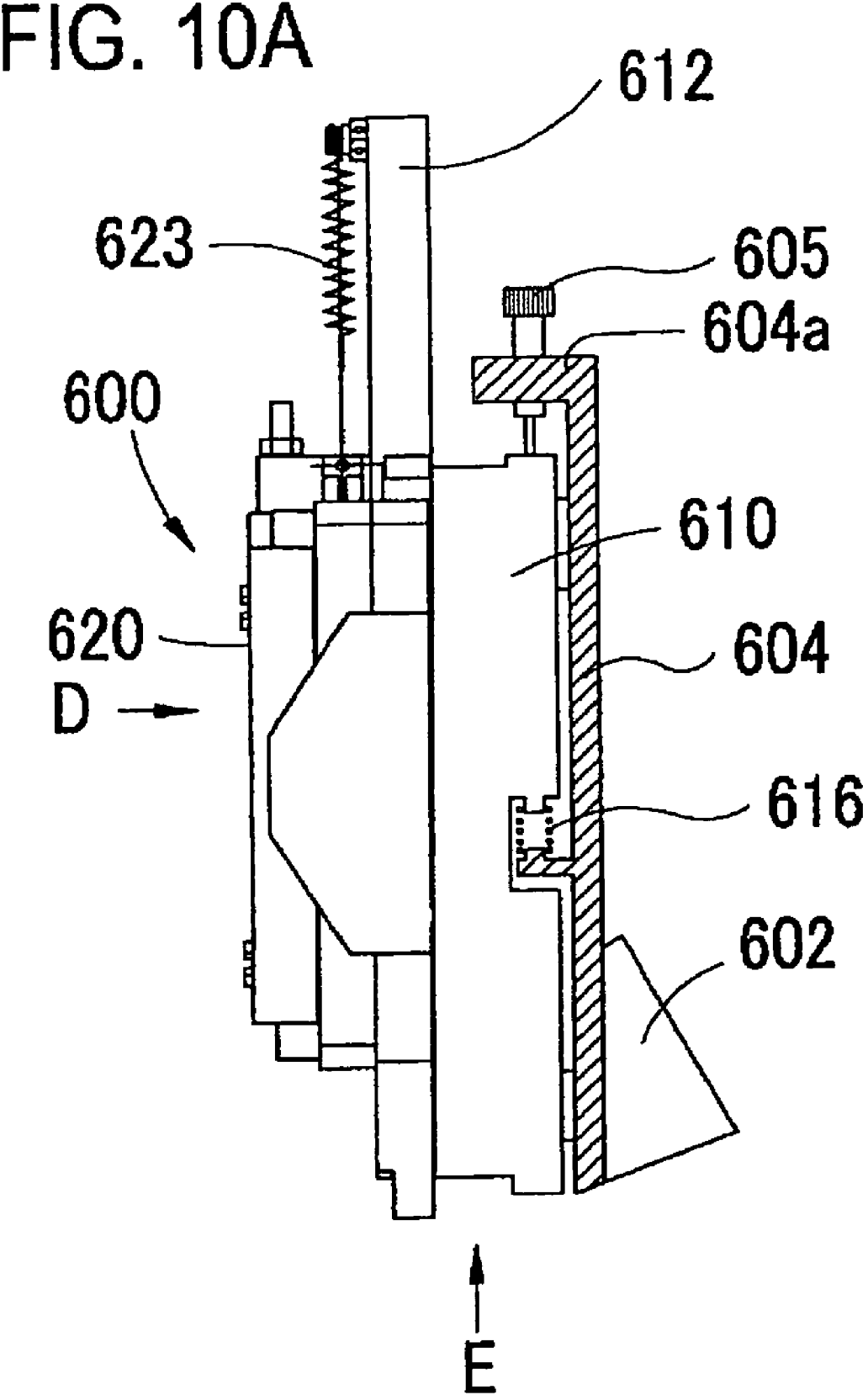
FIG. 10A is an external view showing a schematic configuration of a Z-moving unit.
Figure 10B:
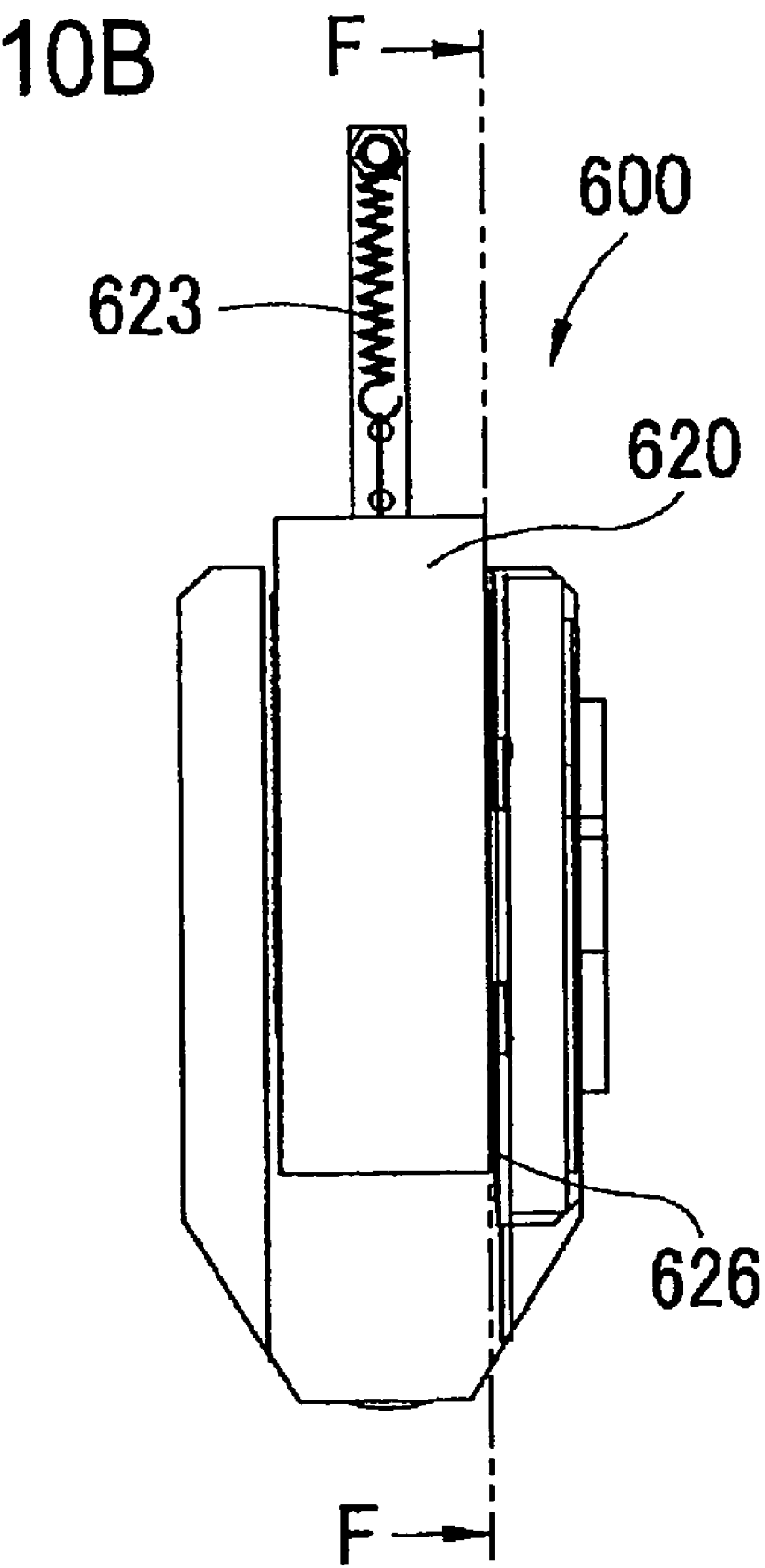
FIG. 10B is another external view showing the schematic configuration of the Z-moving unit.
Figure 10C:
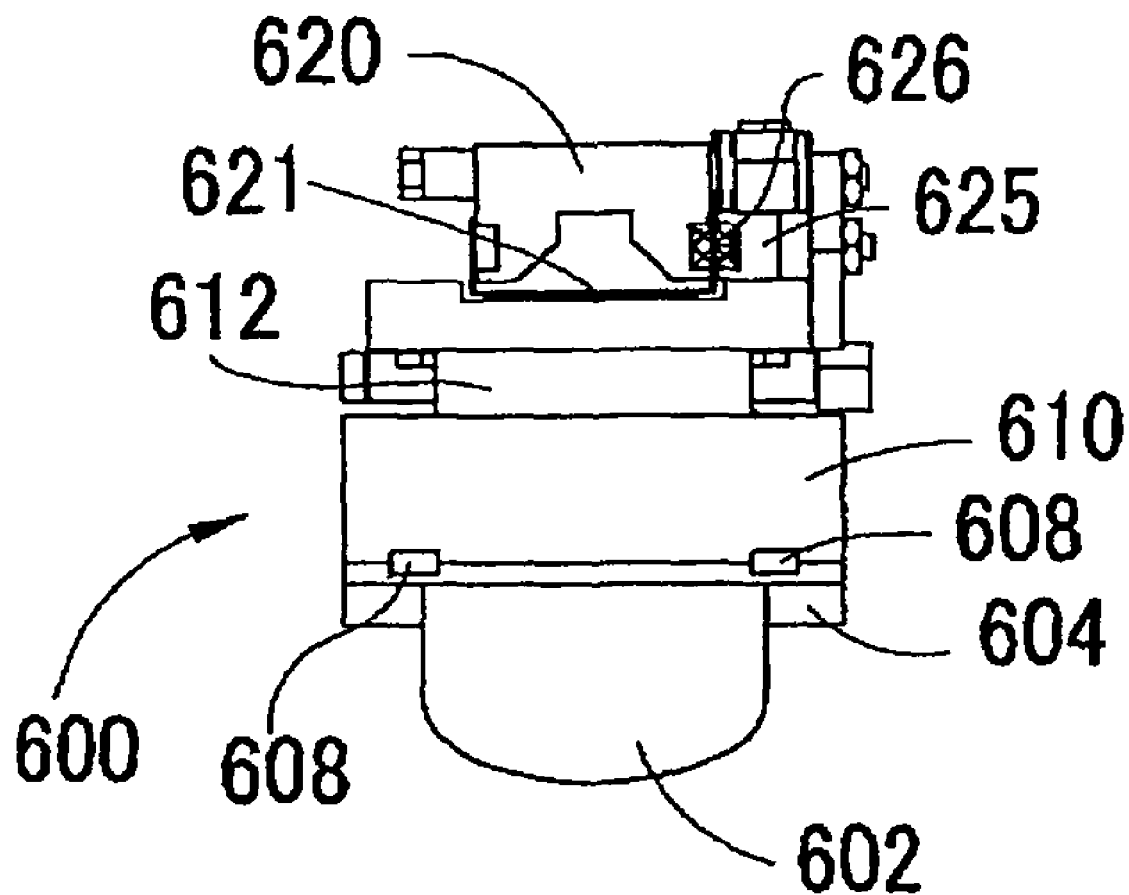
FIG. 10C is another external view showing the schematic configuration of the Z-moving unit.
Figure 10D:
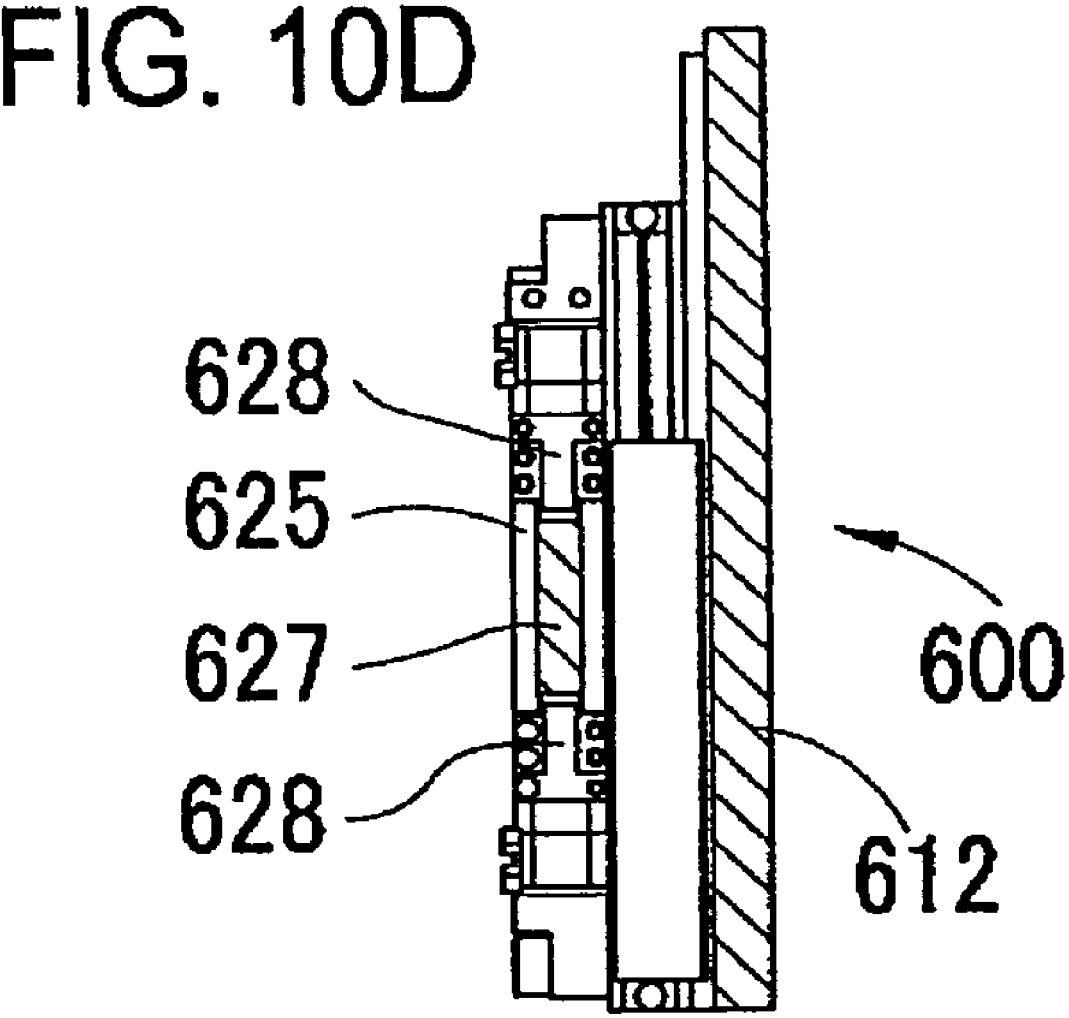
FIG. 10D is another sectional view showing the schematic configuration of the Z-moving unit.

FIG. 9 is a sectional view showing a schematic configuration of the second tilting unit 500 and showing a sectional view of the second tilting unit 500 taken along the Y0-Z0 plane. A second fine-motion shaft 502 is held in a housing 506 through two bearings 504 so as to be coaxial with the second tilt axis YT and rotatable (tiltable) about the second tilt axis YT. On the second fine-motion shaft 502, a brake disk 508 is fixed. Movable brake pads 510a and 510b are placed on both sides of the brake disk 508. The pads 510a and 510b are arranged to be movable in a direction that presses the brake disk 508 through rubber diaphragms 512a and 512b. When compressed air is supplied from the pump 50 through a tube, the diaphragms 512a and 512b are pushed, pressing the pads 510a and 510b against the brake disk 508. The brake disk 508 is thus nipped or caught between the pads 510a and 510b to lock rotation of the second fine-motion shaft 502. When the compressed air from the pump 50 is released or reduced in pressure, the pads 510a and 510b are returned by restoring forces (or negative pressure control) of the diaphragms 512a and 512b, thereby releasing the second fine-motion shaft 502 from a rotation locked state. The compressed air is supplied or released (or reduced in pressure) by operation of the electromagnetic valve 51 controlled by the control unit 20 based on a switch signal (a command signal) of the operation panel 30 or the footswitch 40. Any other device may be adopted for fixing the second fine-motion shaft 502.

On a rear end side of the second fine-motion shaft 502, a second rough-motion member 513 is held in the housing 506 through two bearings 516 so as to be coaxial with the second tilt axis YT and rotatable (tiltable) about the second tilt axis YT. The second fine-motion shaft 502 and the second rough-motion member 513 are configured independently of each other. A rotatable range of the second rough-motion member 513 (a tiltable range of the surgical instrument 10) is determined to be relatively wide and preferably cause the surgical instrument 10 to tilt at a tilt angle of ±45° or more from a vertical position thereof, and more preferably, at a tilt angle of ±60° or more. A brake disk 514 is fixed to the second rough-motion member 513 so as to be independent of the brake disk 508. Furthermore, a fixed brake pad 518a and a movable brake pad 518b are arranged on both sides of the brake disk 514. The pad 518a has been adjusted by an adjustment screw 520 to provide such a slight clearance as not to contact the brake disk 514 when the disk 514 is rotated. The pad 518b is placed to be movable by a rubber diaphragm 522 in a direction that presses the brake disk 514. When compressed air is supplied from the pump 50 through a tube, the diaphragm 522 is pushed, pressing the pad 518b against the brake disk 514. The brake disk 514 is thus nipped or caught between the pads 518a and 518b, thus locking rotation of the second rough-motion member 513. When the compressed air from the pump 50 is released or reduced in pressure, the pad 518b is returned by restoring force (or negative pressure control) of the diaphragm 522, thereby releasing the second rough-motion member 513 from a rotation locked state. The compressed air is supplied and released (or reduced in pressure) by operation of the electromagnetic valve 52 controlled by the control unit 20 based on a switch signal (a command signal) of the operation panel 30 or the footswitch 40. Any other device may be adopted for fixing the second rough-motion member 513.

The second tilting unit 500 is further provided with a mechanism for limiting rotation of the second fine-motion shaft 502 and a mechanism for imparting resistance to damp rotation of the second fine-motion shaft 502. The mechanisms are basically the same those in the first tilting unit 400. Specifically, a flange 530 is fixed to a rear end of the second fine-motion shaft 502 and a flange 540 is fixed to a front end of the second rough-motion member 513. The flange 530 is formed with a hole 532 and the flange 540 is attached with a boss 542 engaging in the hole 532. The hole 532 and the boss 542 serve to limit the rotatable angle of the second fine-motion shaft 502 about the second tilt axis YT to a smaller angle than the rotatable angle of the second rough-motion member 513 and to switch (change) the tiltable range of the surgical instrument 10 in at least two stages; a rough-motion range and a fine-motion range. The hole 532 is larger in diameter than the boss 542. In a clearance between the hole 532 and the boss 542, a viscoelastic member 534 such as silicone resin is inserted to impart resistance in order to make heavier (or damp) the rotation of the second fine-motion shaft 502 (the tilting of the surgical instrument 10). When the second rough-motion member 513 is locked by operation of the electromagnetic valve 52, therefore, the second fine-motion shaft 502 can be rotated only in a deformable range of the viscoelastic member 534. Reaction to the external force also becomes heavier (slow) by the viscoelastic member 534 (resistance is imparted). Thus, fine positioning of the tip end of the surgical instrument 10 can be facilitated. A movable range of the second fine-motion shaft 502 is set as with the movable range of the first fine-motion shaft 404. Specifically, the movable range of the second fine-motion shaft 502 is preferably determined to be within ±5° relative to the locked second rough-motion member 513. When the second rough-motion member 513 is locked and simultaneously the second fine-motion shaft 502 is locked by operation of the electromagnetic valve 51, the surgical instrument 10 is completely held against tilt (rotation) about the second tilt axis YT.

The second tilting unit 500 has a balance mechanism including a spring and other for reducing gravity moment that acts when the surgical instrument 10 is tilted (rotated) about the second tilt axis YT. This balance mechanism may be identical to the balance mechanism of the first tilting unit 400.

FIG. 10 is a view showing a schematic configuration of the Z moving unit 600; FIG. 10(a) is an external view of the Z moving unit 600 seen from side, FIG. 10(b) is an external view seen from a direction D in FIG. 10(a), FIG. 10(c) is an external view seen from a direction E in FIG. 10(a), and FIG. 10(d) is a sectional view along a line F-F in FIG. 10(b).

To the block 602 attached to the second fine-motion shaft 502, a holding base 604 is fixed to extend in the Z-axis direction. On the base 604, a Z fine-motion block 610 is held through linear-motion bearings 608 so as to be movable in the Z axis direction. An upper end 604a of the base 604 is attached with a micrometer 605. The Z fine-motion block 610 is pressed (urged upward) toward the micrometer 605 by a spring 616 interposed between the block 610 and the base 604. Accordingly, when the micrometer 605 is operated, the Z fine-motion block 610 is quantitatively finely adjusted in the Z axis direction. The positions of the micrometer 605 and the spring 616 may be vertically interchanged each other.

On a holding base 612 fixed to the Z fine-motion block 610, a Z rough-motion block 620 is held to be movable in the Z axis direction through a linear-motion shaft 621 of a cross roller type. The Z rough-motion block 620 suspends from the base 612 by a tension spring 623 to reduce downward load resulting from own weight. In a holder 625 placed on each side of the Z rough-motion block 620, a tube 626 which will pneumatically expand is set. From above, a movable brake pad 627 is placed to cover an opening of the holder 625 and the pad 627 is retained by leaf springs 628. When compressed air is supplied from the pump 50 to the tube 626, the Z rough-motion block 620 is held and locked between the pads 627. This lock of the Z rough-motion block 620 is also performed by operation of an electromagnetic valve controlled by the control unit 20 based on a switch signal (a command signal) of the operation panel 30 or the footswitch 40. Any other device may also be adopted for fixing the Z rough-motion block 620.

Figure 11A:
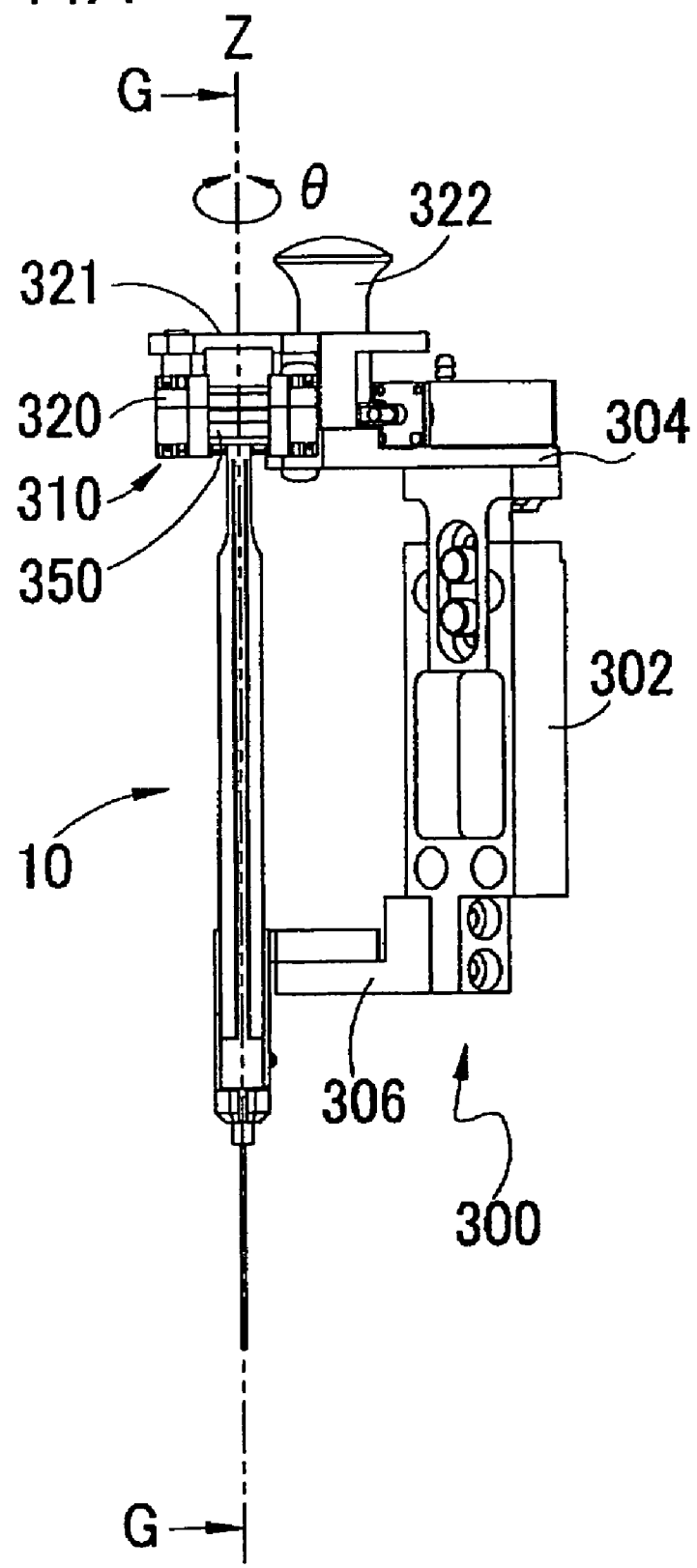
FIG. 11A is an external view showing a schematic configuration of a holding unit of a surgical instrument.
Figure 11B:
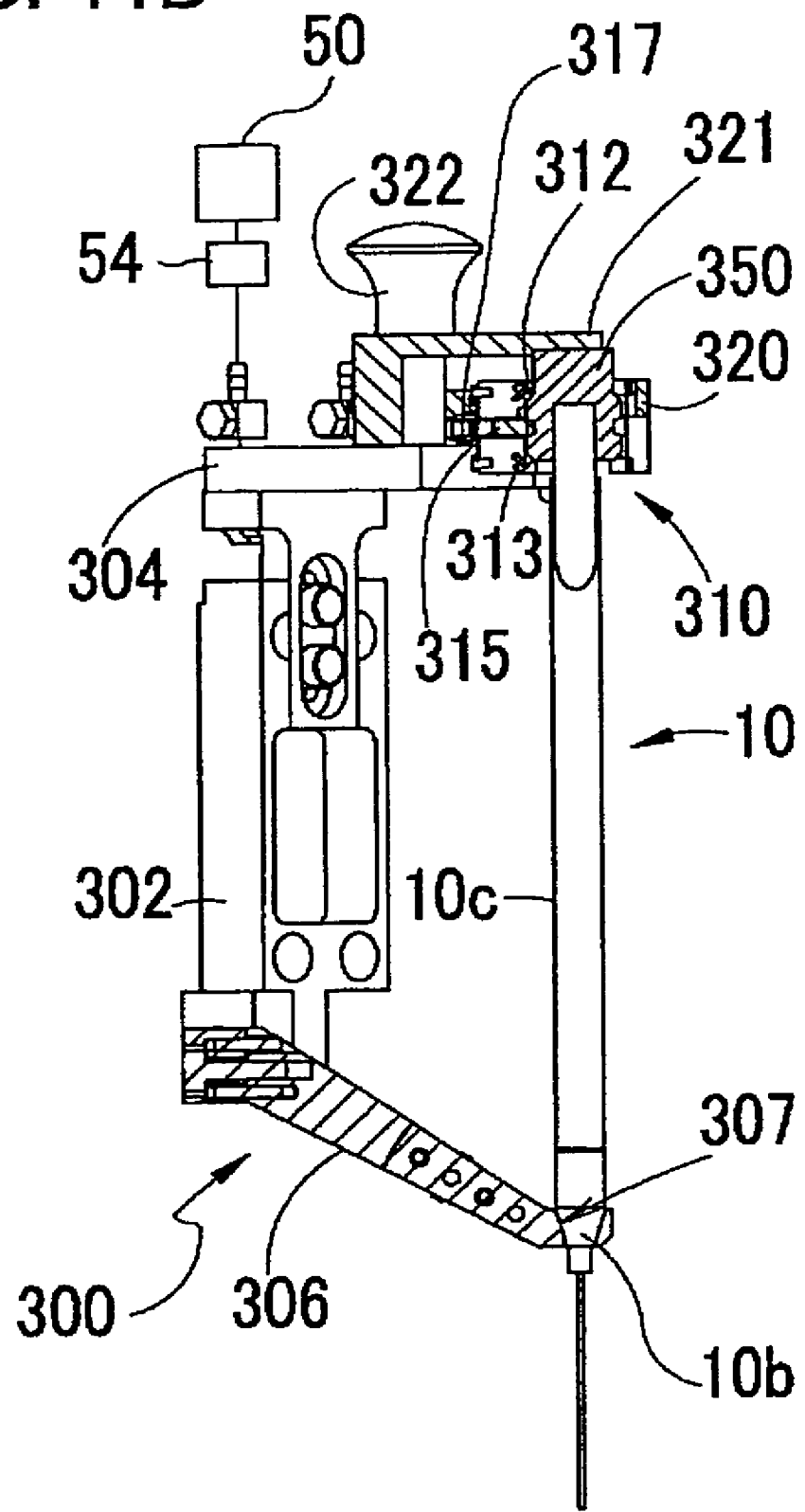
FIG. 11B is another sectional view showing the schematic configuration of the holding unit of the surgical instrument.
Figure 12:
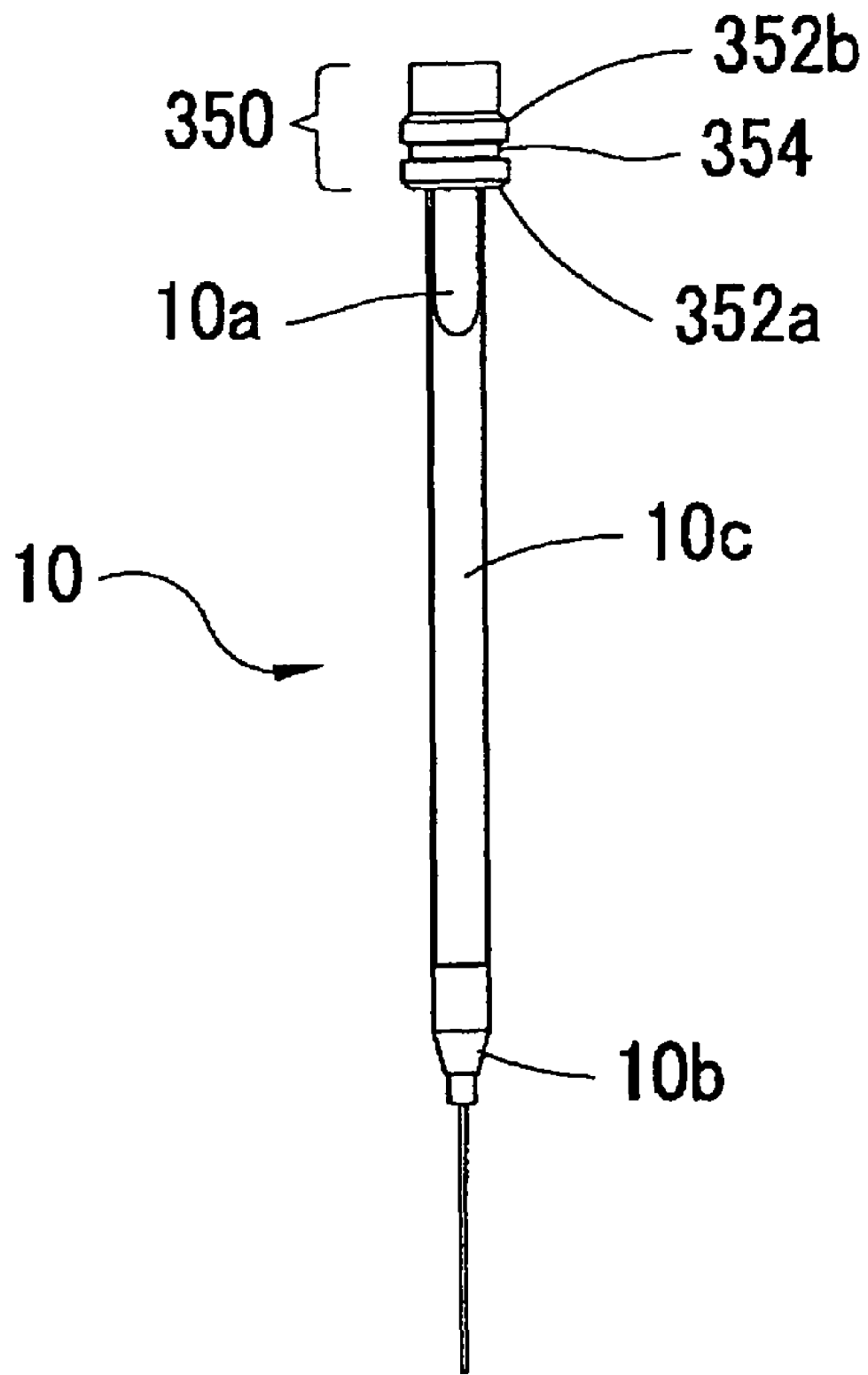
FIG. 12 is a view showing an adaptor to mount the surgical instrument in the holding unit.

FIG. 11 is a view showing a schematic configuration of the holding unit 300; FIG. 11(a) is an external view of the holding unit 300 attached with the surgical instrument 10, seen from side and FIG. 11(b) is a sectional view of the same along a ling G-G in FIG. 11(a). FIG. 12 is a view showing an adaptor 350 for mounting the surgical instrument 10 in the holding unit 300.

The adaptor 350 is attached to a rear end of the surgical instrument 10 and held against rotation. A side surface of the rear end of the surgical instrument 10 is formed with a flat face 10a. The adaptor 350 is formed with a hole shaped to conform to the shape of the flat face 10a of the surgical instrument 10. Accordingly, the rear end of the surgical instrument 10 can be inserted easily in the hole of the adaptor 350. The adaptor 350 is formed with a first rotation rail 352a and a second rotation rail 352b which are supported by bearings 312 and 313 when the adaptor 350 is set in the holding unit 300. Between the first and second rotation rails 352a and 352b, a friction groove 354 is formed in which a brake pad 315 will be pressed.

On the holding base 302, the Z rough-motion block 620 is fixed. A holding arm 304 is connected to an upper end of the base 302 and a holding arm 306 is connected to a lower end of the base 302. The arm 306 is formed, at its distal end, with an insertion hole 307 which receives a tapered portion 10b of the surgical instrument 10. The hole 307 is preferably made of a material causing less frictional resistance. Between the based 302, the arm 304, and the arm 306, sufficient spaces are provided to allow the operator to grip a main part 10c of the surgical instrument 10.

The arm 304 is provided with a holding part 310 for rotatably holding the adaptor 350 attached to the rear end of the surgical instrument 10. The holding part 310 has three bearings 312 arranged at 120° intervals so as to rotatably hold the first rotation rail 352a. The holding part 310 further has a brake pad 315 which will be pressed against the groove 354. The pad 315 is pressed against the groove 354 by a cylinder rod 317 which is activated by compressed air supplied from the pump 50 through the electromagnetic valve 54 and a tube, thereby locking the rotation of surgical instrument 10 about the Z axis. When the compressed air from the pump 50 is released or reduced in pressure by operation of the electromagnetic valve 54 controlled by the control unit 20 based on a switch signal (a command signal) of the operation panel 30 or the footswitch 40, the cylinder rod 317 is moved to return the pad 315, thereby unlocking the rotation of the surgical instrument 10 about the Z axis. Any other device for fixing the adaptor 350 may also be adopted.

To adjust locking strength and response time, a speed controller not shown is placed between the electromagnetic valve 54 and a brake unit constituted of the cylinder rod 317 and others.

The holding part 310 is supported by an adaptor retaining plate 320 and a pressurizing plate 321 which serve to prevent the adaptor 350 from dropping off. The retaining plate 320 has three bearings 313 arranged at 120° intervals so as to rotatably hold the second rotation rail 352b. The retaining plate 320 and the pressurizing plate 321 are integral with each other through a spring. The retaining plate 320 and the pressurizing plate 321 are pressed toward the arm 304 by an appropriate force of the screw 322, thereby preventing excessive load from acting on the bearings 312 and 313. When the screw 322 is loosened, the retaining plate 320 and the pressurizing plate 321 can be detached from the holding part 310. In such a way, the adaptor 350 attached to the surgical instrument 10 can be mounted in the holding part 310. After the adaptor 350 is mounted in the holding part 310, the retaining plate 320 and the pressurizing plate 321 are attached again and the screw 322 is tightened. The adaptor 350 is thus held in the holding part 310.

The control unit 20 is connected to the operation panel 30 having a plurality of switches, a display, and others, the footswitch 40 for inputting a plurality of operation signals, the rough adjustment unit 150, the pump 50, each electromagnetic valve, and others.

Figure 13:
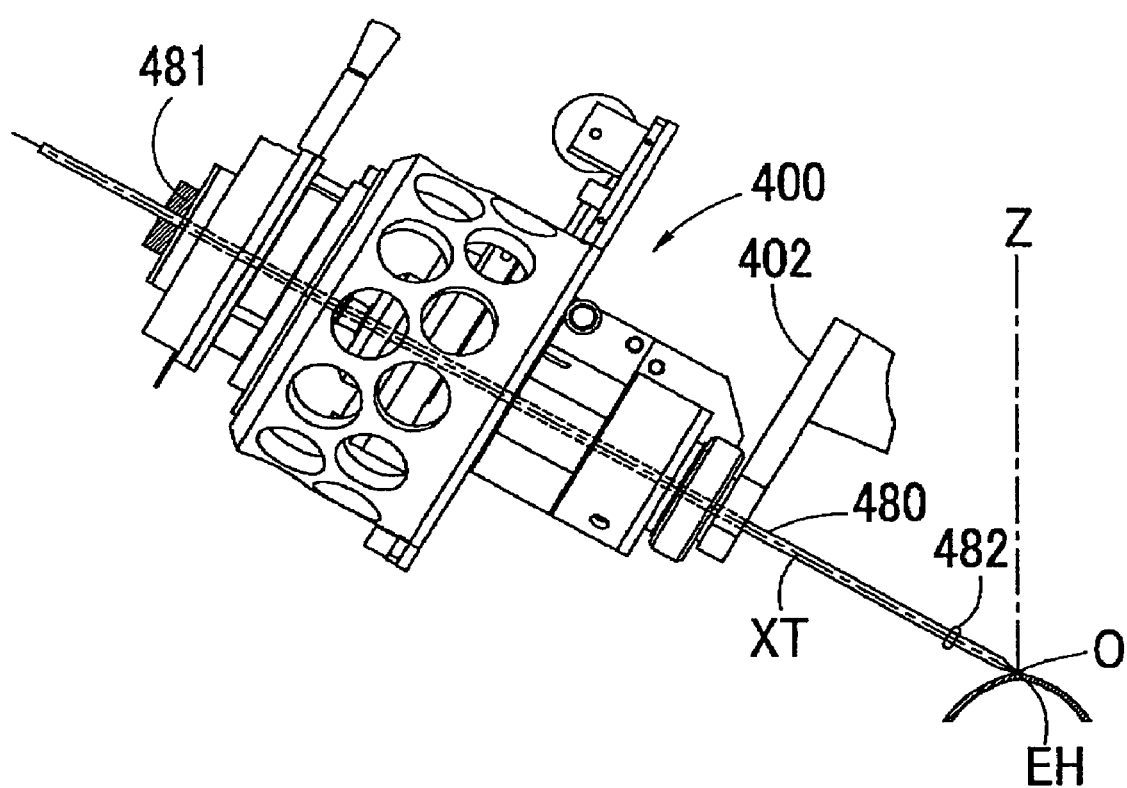
FIG. 13 is a view to explain positioning of a tilt center point to a wound opening formed in a sclera.

Next, operations of the surgery support device 1 are explained below. As shown in FIG. 13, firstly, the rough adjustment unit 150 and the fine adjustment unit 110 are activated to position the point O of the positioning unit 200 to a wound opening EH (or a portion in which a wound opening is to be formed) formed in a sclera of a patient's eye by another incision surgical instrument. This positioning is conducted before the surgical instrument 10 is mounted in the holding unit 300. To position the point O to the wound opening EH, the shaft 480 serving as a positioning device is inserted in advance in each hollow part of the first fine-motion shaft 404 and the first rough-motion shaft 420. A stopper 481 is fixed to the rear end of the shaft 480 so that the tip end of the shaft 480 coincides with the point O. By operation of the rough adjustment unit 150 and the fine adjustment unit 110, the tip end of the shaft 480 is made to coincide with the wound opening EH. The point O is thus positioned to the wound opening EH. After positioning, the shaft 480 is removed from the first fine-motion shaft 404 and the first rough-motion shaft 420 (or is pulled upward and stopped by an O ring 482 so as not to be an obstacle).

As the positioning unit for positioning the point O to the wound opening EH, the shaft 480 is held in the first tilting unit 400. The shaft 480 may be held in a special holding mechanism additionally provided in the positioning unit 200. Instead of using the shaft 480, a configuration for optically positioning the point O to the wound opening EH may be adopted. For instance, a projection optical system may be provided to project light beams from two directions to the wound opening EH of the sclera and arranged to adjust the light beams from two directions to coincide with each other at the point O. The light beams are projected from two directions toward the wound opening EH of the sclera and the positioning unit 200 is moved to direct the two light beams to the same location, thereby positioning the point O to the wound opening EH.

Figure 14B:
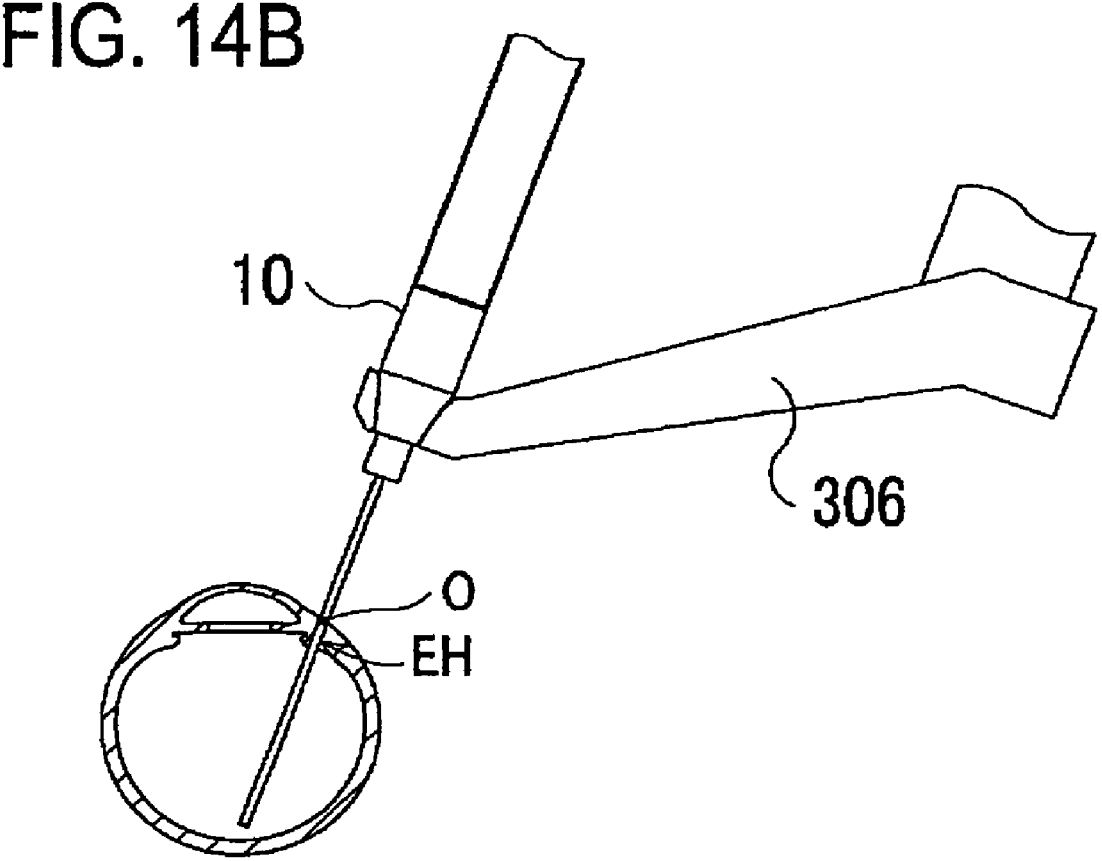
FIG. 14B is another view to explain operations in the surgery.

After completion of the positioning of the point O to the wound opening EH, as mentioned above, the surgical instrument 10 is mounted in the holding unit 300. When the surgical instrument 10 is to be mounted, the Z rough-motion block 620 is moved upward and fixed. After the surgical instrument 10 is mounted in the holding unit 300, the Z rough-motion block 620 is released from a fixed state. The tip end of the surgical instrument 10 is moved toward the point O as shown in FIG. 14(a). Then, the surgical instrument 10 is moved in the Z axis direction and inserted into the eye as shown in FIG. 14(b).

The surgical instrument 10 is operated to position the tip end of the surgical instrument 10 in an affected part of the fundus or another site under observation through a microscope. The surgical instrument 10 is held by the first tilting unit 400 and the second tilting unit 500 so as to tilt in two dimensions about the point O. The surgical instrument 10 is also held by the Z moving unit 600 so as to move in the Z axis direction. At that time, the point O coincides with the wound opening EH. Accordingly, the tip end of the surgical instrument 10 can be moved easily within the eye without widening the wound opening or damaging the sclera.

Furthermore, reaction force of the eyeball to the surgical instrument 10 is reduced. Furthermore, the balance mechanisms for reducing operation force (allowing an easy operation) are provided to the operation shafts which will be influenced by gravity moment acting on the second tilting unit 500, the holding unit 300, and others during movement of the surgical instrument 10. Thus, the surgical instrument 10 can be operated smoothly.

When the tip end of the surgical instrument 10 is to be positioned to the affected part of the patient's eye, the operator observes the affected part from just above through the microscope. At that time, as shown in FIG. 14(b), the surgical instrument 10 is held obliquely in the eye, that is, the holding mechanisms such as the first tilting unit 400 and the second tilting unit 500 are located outside an observation viewing field. Accordingly, the tip end of the surgical instrument 10 can be easily visually recognized.

An explanation is given to an example of an intraocular operation in which a tip end of a surgical instrument is positioned to a fine location in an eye fundus by inserting a catheter into a blood vessel of 0.1 to 0.2 mm in the eye fundus. An affected part of the fundus is observed through the microscope and the surgical instrument 10 is tilted in two dimensions and moved in the Z axis direction. When the tip end of the surgical instrument 10 comes close to a target location, a brake command signal for first rough-motion tilting to be performed by the first tilting unit 400 and a brake command signal for second rough-motion tilting to be performed by the second tilting unit 500 are inputted by the operation panel 30 or the footswitch 40. Based on those signals, the brake mechanisms for the first rough-motion tilting and the second rough-motion tilting are driven under control by the control unit 20 to lock the rotation of each of the first and second rough-motion shafts 420 and 513. Thus, the tilting of the surgical instrument 10 is limited in a narrow range where the first and second fine-motion shafts 404 and 502 are rotated (that is, the XY movable range of the tip end of the surgical instrument 10 is switched (changed) to a range for fine adjustment). Simultaneously, a motion for tilting the surgical instrument 10 is made heavy (damp) by the resistance imparting means such as the viscoelastic members 443 and 534 and others. Accordingly, a precise positioning operation can be carried out easily. The first rough-motion tilting and the second rough-motion tilting can be selectively locked.

According to the tilt range switching mechanism of the first tilting unit 400 and the second tilting unit 500, when the first rough-motion tilting and the second rough-motion tilting are locked after the surgical instrument 10 is tilted at an arbitrary angle, fine-motion tilting is allowed in a narrow range in which a tilt angular position at which the tilting is locked is assumed to be a reference (neutral) position. Therefore, the precise positioning operation can be conducted more easily.

After completion of the positioning of the tip end of the surgical instrument 10 to the blood vessel in the fundus, a brake command signal for first fine-motion tilting to be performed by the first tilting unit 400 and a brake command signal for second fine-motion tilting to be performed by the second tilting unit 500 are inputted by the operation panel 30 or the footswitch 40. Based on those signals, the brake mechanisms for the first fine-motion tilting and the second fine-motion tilting are driven under control by the control unit 20 to lock the rotation of each of the first and second fine-motion shafts 404 and 502. Thus, the tilt of the surgical instrument 10 is completely fixed. The first fine-motion tilting and the second fine-motion tilting are selectively locked. Furthermore, a brake command signal for Z movement to be performed by the Z moving unit 600 is inputted by the operation panel 30 or the footswitch 40. Based on this signal, the brake mechanism for Z movement is driven under control by the control unit 20 to allow only fine adjustment (fine motion) in the Z axis direction to be performed by the micrometer 605. It is difficult to microscopically observe a location of the blood vessel of the fundus in which the tip end of the surgical instrument 10 is inserted. However, the tip end of the surgical instrument can be fine moved quantitatively in the Z axis direction by operation of the micrometer 605, thereby facilitating the precise positioning operation.

As the surgical instrument 10, various kinds of instrument such as forceps, scissors, tweezers, and a vitreous body cutter may be attached. In this case, the adaptor 350 has only to be provided with a hole shaped to conform to the shape of the rear end of the surgical instrument 10. When the position of the holding arm 304 attached to the base 302 is adjustable in the Z axis direction, another surgical instrument 10 different in length can also be attached.

The positioning of the point O to the wound opening EH may also be performed as follows. For instance, the surgical instrument 10 is attached in advance to the holding unit 300. The shaft 480 is inserted in advance in the first fine-motion shaft 404 and the first rough-motion shaft 420. The surgical instrument 10 is then moved in the Z axis direction to place the tip end of the surgical instrument 10 so as to coincide with the tip end of the shaft 480. Accordingly, the tip end of the surgical instrument 10 is made to coincide with the point O. After the tip end of the surgical instrument 10 coincides with the point O, the compressed air is supplied from the pump 50 to lock the movement of the surgical instrument 10 in the Z axis direction. To position the tip end of the surgical instrument 10 to the wound opening EH, the positioning unit 200 is moved by the rough adjustment unit 150 and the fine adjustment unit 110.

The surgical instrument 10 is operated by being held by hand and therefore the brake signals for the first tilting unit 400, the second tilting unit 500, and the Z moving unit 600 are preferably entered by the footswitch 40. In many cases, a different ophthalmic apparatus is used together in an operation room. When the footswitch 40 is used in common as a footswitch of the other ophthalmic apparatus, accordingly, any complicated works for a plurality of footswitches such as replacement, selective use, and others can be eliminated advantageously.

Figure 15:
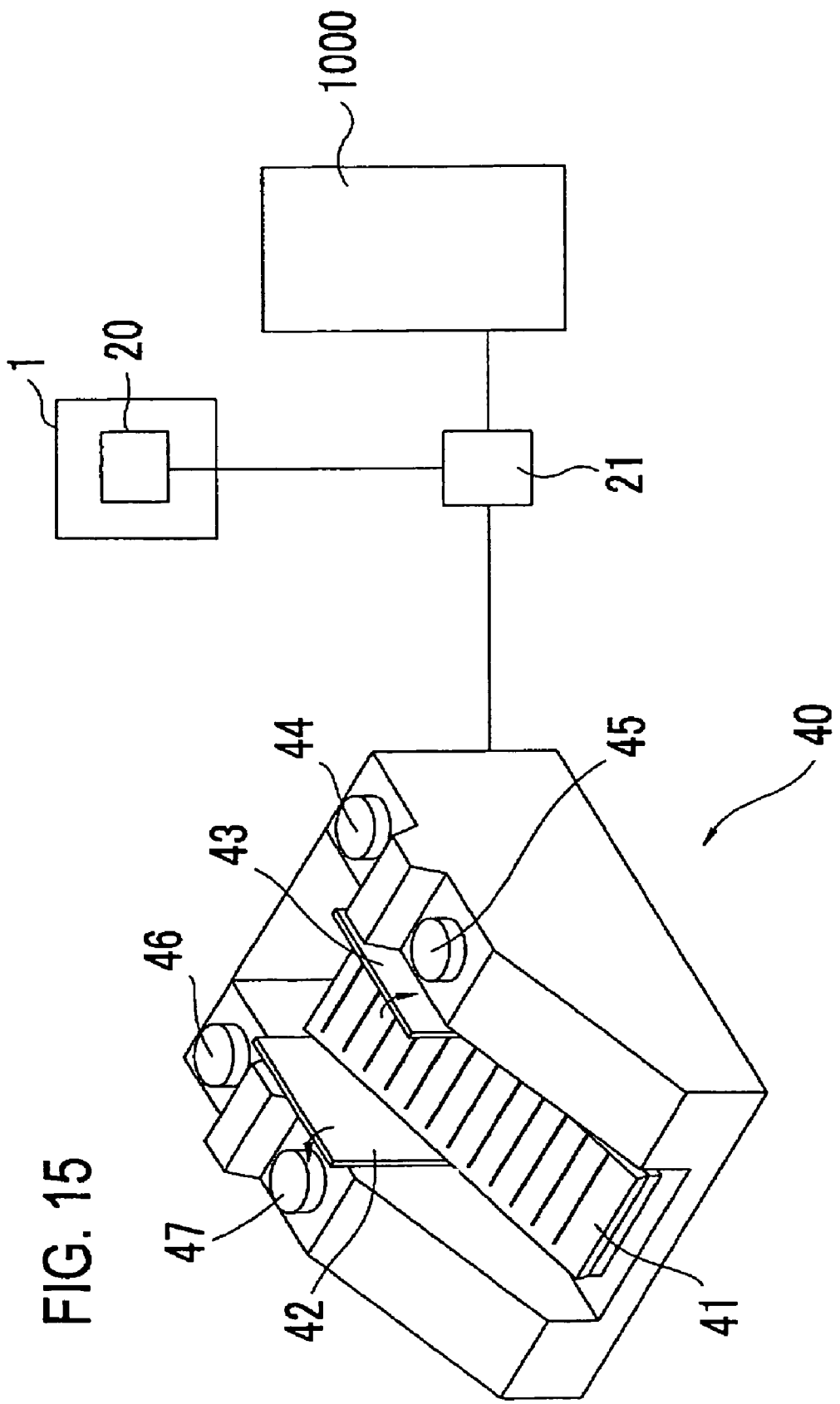
FIG. 15 is a schematic configuration view of a footswitch of a surgery support device is used in common as a footswitch of another ophthalmic apparatus.

FIG. 15 is a schematic configuration view showing the case where the footswitch of the surgery support device 1 and a footswitch of another ophthalmic apparatus are used in common. The other ophthalmic apparatus in this embodiment is a cataract surgery apparatus 1000. This surgery apparatus 1000 is arranged to amplify and transmit ultrasonic vibration to a chip attached to the tip end of a hand piece, crush and emulsify a nucleus lentis clouded due to cataract, and suck and remove it together with perfusate supplied in the eye. In this surgery apparatus 1000, similarly, the footswitch is used to input each operation signal for supply of the perfusate in the eye, suction of waste liquid from the eye, and ultrasonic vibration. The footswitch 40 includes a first switch 41 provided in the center, a second switch 42 and a third switch 43 provided on either side of the first switch 41, a fourth switch 44, a fifth switch 45, a sixth switch 46, and a seventh switch 47 which are placed at four corners of an upper surface of a casing of the footswitch. In the surgery apparatus 1000, those seven switches are assigned to input of the signals for supply of the perfusate, suction of waste liquid, and ultrasonic vibration. When the footswitch 40 is to be used for the surgery support device 1, a signal switching section 21 switches connection of the footswitch 40 from the surgery apparatus 1000 to the surgery support device 1 (the control unit 20).

The seven switches of the footswitch 40 are assigned as follows, for example. Every time the switch 46 is pressed, a brake signal for the first rough-motion tilting, a brake signal for the first fine-motion tilting, and a release signal of each brake are inputted in sequence. Every time the switch 44 is pressed, a brake signal for the second rough-motion tilting, a brake signal for the second fine-motion tilting, and a release signal of each brake are inputted in sequence. Every time the switch 47 is pressed, a brake signal for Z movement and a release signal of the brake are inputted in sequence. Furthermore, every time the switch 45 is pressed, a brake signal for rotation about the Z axis and a release signal of the brake are inputted in sequence. When the switch 42 is pressed, all the brake signals and respective brake release signals are inputted in sequence. Every time the switch 43 is pressed, a brake signal for all of the rough-motion tilting and respective brake release signals are inputted in sequence. Every time the switch 41 is pressed, a brake signal for all of the fine-motion tilting and respective brake release signals are inputted in sequence.

The above explanation is given to the configuration that the surgical instrument 10 is manually operated by the operator. As an alternative, the first fine-motion shaft 404 and the second fine-motion shaft 502 and/or the micrometer 605 may be electrically operated. In this case, the surgical instrument 10 can be finely positioned with higher precision.

The invention claimed is:

1. An ophthalmic surgery support device for assisting an operator in an operation of a surgical instrument in order to position a tip end of the surgical instrument to be inserted in an eye through a wound opening formed in an eyeball of a patient to a fine location in the eye, the device comprising:
    a moving mechanism for holding the surgical instrument movably in a Z axis direction that is a longitudinal direction of the surgical instrument to be inserted in the eye;
    a tilting mechanism for holding the moving mechanism so that the surgical instrument is tiltable in an arbitrary direction about a predetermined point which is located on a Z axis and is positioned to the wound opening; and
    a tilt locking mechanism for locking tilt of the surgical instrument tilted by the tilting mechanism,
    wherein the tilting mechanism comprises:
    a rough-motion tilting mechanism;
    a fine-motion tilting mechanism providing a finer tilt range than the rough-motion tilting mechanism;
    a tilt switching mechanism for switching tilt of the surgical instrument by the rough-motion tilting mechanism to tilt of the surgical instrument by the fine-motion tilting mechanism; and
    a resistance imparting means for imparting resistance to make a tilting operation of the surgical instrument by the fine-motion tilting mechanism heavier than a tilting operation of the surgical instrument by the rough-motion tilting mechanism.

2. The ophthalmic surgery support device according to claim 1, wherein
    the tilt locking mechanism comprises a rough-motion-tilting locking mechanism for locking the tilt of the surgical instrument tilted by the rough-motion tilting mechanism; and
    a fine-motion-tilting locking mechanism for locking the tilt of the surgical instrument tilted by the fine-motion tilting mechanism,
    the tilt switching mechanism for switching the tilt of the surgical instrument by the rough-motion tilting mechanism to the tilt of the surgical instrument by the fine-motion tilting mechanism when the tilt of the surgical instrument is locked by the rough-motion-tilting locking mechanism.

3. The ophthalmic surgery support device according to claim 2, wherein
    the tilting mechanism comprises a first tilting mechanism for holding the moving mechanism so as to tiltable about a first axis passing the predetermined point, and a second tilting mechanism for holding the first tilting mechanism so as to tiltable about a second axis intersecting the first axis at the predetermined point,
    the tilt locking mechanism comprises a first tilt locking mechanism for locking the tilt of the surgical instrument tilted by the first tilt mechanism and a second tilt locking mechanism for locking the tilt of the surgical instrument tilted by the second tilting mechanism,
    each of the first and second tilting mechanisms includes the rough-motion tilting mechanism, the fine-motion tilting mechanism, the tilt switching mechanism, and the resistance imparting means, and
    each of the first and second tilt locking mechanism has a rough-motion-tilting locking mechanism and a fine-motion-tilting locking mechanism.

4. The ophthalmic surgery support device according to claim 2, wherein
    at least one of the rough-motion-tilting locking mechanism and the fine-motion-tilting locking mechanism includes a brake mechanism utilizing pressure of air from a pump.

5. The ophthalmic surgery support device according to claim 2, further comprising a signal input unit for inputting a command signal to operate each of the rough-motion-tilting locking mechanism and the fine-motion-tilting locking mechanism, and
    a control unit for controlling operation of each locking mechanism based on the command signal from the signal input unit.

6. The ophthalmic surgery support device according to claim 5, wherein
    the signal input unit includes a footswitch provided with a plurality of switches, and
    the footswitch is used in common as a footswitch of a different ophthalmic apparatus.

7. The ophthalmic surgery support device according to claim 1, wherein
    the moving mechanism comprises:
    a rough-motion moving mechanism;
    a fine-motion moving mechanism for providing a finer movable range than the rough-motion moving mechanism; and
    a movement switching mechanism for switching movement of the surgical instrument by the rough-motion moving mechanism to movement of the surgical instrument by the fine-motion moving mechanism.

8. The ophthalmic surgery support device according to claim 1, further comprising:
    a rotating mechanism for holding the surgical instrument so as to be rotatable about the Z axis; and
    a rotation locking mechanism for locking the rotation of the surgical instrument.

9. The ophthalmic surgery support device according to claim 1, further comprising
    a three-dimensional moving mechanism for moving the tilting mechanism in three dimensions.

* * * * *